United States Patent
Casu et al.

(10) Patent No.: US 7,781,416 B2
(45) Date of Patent: Aug. 24, 2010

(54) DERIVATIVES OF PARTIALLY DESULPHATED GLYCOSAMINOGLYCANS AS HEPARANASE INHIBITORS, ENDOWED WITH ANTIANGIOGENIC ACTIVITY AND DEVOID OF ANTICOAGULATING EFFECT

(75) Inventors: Benito Casu, Milan (IT); Giangiacomo Torri, Milan (IT); Anna Maria Naggi, Milan (IT); Giuseppe Giannini, Pomezia (IT); Claudio Pisano, Pomezia (IT); Sergio Penco, Milan (IT)

(73) Assignee: Sigma-Tau Research Switzerland S.A., Lugano (CH)

( * ) Notice: Subject to any disclaimer, the term of this patent is extended or adjusted under 35 U.S.C. 154(b) by 0 days.

(21) Appl. No.: 11/314,736

(22) Filed: Dec. 22, 2005

(65) Prior Publication Data

US 2006/0172968 A1    Aug. 3, 2006

Related U.S. Application Data

(63) Continuation-in-part of application No. 10/489,359, filed on Feb. 2, 2005, now abandoned, and a continuation-in-part of application No. 11/028,512, filed on Jan. 4, 2005, which is a continuation-in-part of application No. 10/967,255, filed on Oct. 19, 2004, now abandoned, which is a continuation-in-part of application No. 10/182,185, filed on Jul. 25, 2002, now abandoned.

(51) Int. Cl.
*A61K 31/727* (2006.01)
*A61K 31/737* (2006.01)

(52) U.S. Cl. .......................... 514/54; 514/56; 536/18.7; 536/21; 536/55.3

(58) Field of Classification Search ................. 514/54, 514/56; 536/18.7, 21, 55.3
See application file for complete search history.

(56) References Cited

U.S. PATENT DOCUMENTS

| | | | |
|---|---|---|---|
| 4,500,519 A | | 2/1985 | Lormeau et al. |
| 4,990,502 A | * | 2/1991 | Lormeau et al. ............. 514/56 |
| 5,280,016 A | * | 1/1994 | Conrad et al. ............... 514/56 |
| 5,583,121 A | * | 12/1996 | Chaudry et al. ............. 514/56 |
| 5,808,021 A | | 9/1998 | Holme et al. |
| 5,854,221 A | * | 12/1998 | Cao et al. .................... 514/12 |
| 5,912,237 A | | 6/1999 | Kennedy |
| 2002/0010152 A1 | | 1/2002 | DeAmbrosi et al. |

FOREIGN PATENT DOCUMENTS

| | | |
|---|---|---|
| EP | 0 254 067 A | 1/1988 |
| WO | 88/01280 A | 2/1988 |
| WO | 92/01003 A | 1/1992 |
| WO | 94/14851 A | 7/1994 |
| WO | 95/02613 A | 1/1995 |
| WO | 96/06867 A | 3/1996 |
| WO | 99/27976 | 6/1999 |
| WO | 01/55221 A | 8/2001 |

OTHER PUBLICATIONS

The Merck Manual 16th Ed., 1999, pp. 339-342 and 1488-1489.*
Goodman and Gilman's "The Pharmacological Basis of Therapeutics", 10th Ed., 1996, p. 54-57.*
Lewis et al FEBS Letters, 1979, 97(1), 119-123.*
Sjoberg et al Carbohydrate Research, 1980, 80, 131-145.*
Zoppetti et al Arzheim.-Forsch./Drug Res. 1986, 36(1), 637-642.*
Edovitsky et al, "Blood", 1, vol. 107, No. 9, pp. 3609-3616, May 2000.
Fransson, L., et al, "Periodate and alkaline degradation of heparin-related glycans" Carbohyd. Res. (1980) vol. 80, pp. 131-145.
Fransson, L., et al "Relationship between anticoagulant activity of heparin and susceptibility to periodate oxidation" FEBS Lett. (1979) vol. 97, No. 1, pp. 119-123.
Casu, B., et al, "Retention of Antilipemic activity by periodate-oxidized non-anticoagulant heparins" Arzneim.-Forsch./Drug Res., vol. 36, No. 1, pp. 637-642, 1986.
Zoppetti et al Arzheim-Forsch./Drug Res. 1986, 36(1), 637-642.

* cited by examiner

*Primary Examiner*—Shaojia Anna Jiang
*Assistant Examiner*—Ganapathy Krishnan
(74) *Attorney, Agent, or Firm*—Lucas & Mercanti, LLP

(57) ABSTRACT

Partially desulphated glycosaminoglycan derivatives are described, particularly heparin, and more particularly a compound of formula (I)

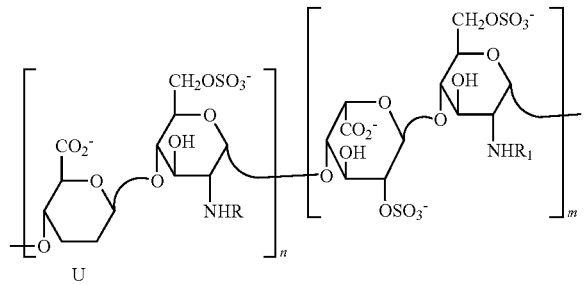

where the U, R and $R_1$ groups have the meanings indicated in the description. These glycosaminoglycan derivatives have antiangiogenic and heparanase-inhibiting activity and are devoid of anticoagulant activity.

10 Claims, 10 Drawing Sheets

13C NMR spectra

13C NMR spectra

13C NMR spectra

A = fully N-acetylated heparin
(a) = before incubation with heparanase
(b) = after incubation with heparanase B = 52% glycol split
(a) = before incubation with heparanase
(b) = after incubation with heparanase

DERIVATIVES OF PARTIALLY DESULPHATED GLYCOSAMINOGLYCANS AS HEPARANASE INHIBITORS, ENDOWED WITH ANTIANGIOGENIC ACTIVITY AND DEVOID OF ANTICOAGULATING EFFECT

CROSS-REFERENCE TO RELATED APPLICATIONS

This application is a continuation-in-part of application Ser. No. 10/489,359 filed Feb. 2, 2005 now abandoned. It is also a continuation-in-part of application Ser. No. 11/028,512 filed Jan. 4, 2005 which in turn is a continuation-in-part of Ser. No. 10/967,255 filed Oct. 19, 2004 (now abandoned) which is a continuation-in-part of Ser. No. 10/182,185 filed Jul. 25, 2002 (now abandoned).

The invention described herein relates to partly desulphated glycosaminoglycan derivatives, particularly heparins, to processes for their preparation, to their use as active ingredients for the preparation of medicaments useful in pathological conditions, like tumors, included the metastatic forms, and for any therapeutic indication gaining benefit from the inhibition of the heparanase, and to pharmaceutical compositions containing them.

BACKGROUND OF THE INVENTION

Studies performed in the Tumor Biological Research Unit of the Hadassah-Hebrew University Hospital-Israel (*Isr. Med. Assoc. J.* 2000, 2, 37-45; *J. Med. Chem.* 2000, 43, 2591-600; *Invasion Metastasis* 1994-95, 14, 290-302; *Exp. Cell Res.* 1992, 201, 208-15) focus on the involvement of heparin-binding growth factors, heparan sulphate and heparan sulphate-degrading enzymes (heparanase) in tumor angiogenesis and metastasis. These studies have been applied to screening and to the identification of heparin derivatives and heparin/heparan sulphate mimetics with potent heparanase inhibiting activity (*Nature Med.* 1999, 5, 735-6; *Science*, 1999, 285, 33-4].

Tumor cells release the enzyme heparanase, an endo-□-D-glucuronidase which degrades the polysaccharide chain of heparan sulphate proteoglycans on cell surfaces and in the extracellular matrix.

Involvement in tumor angiogenesis of heparanase has been correlated with the ability to release bFGF (FGF-2) and other growth factors from its storage within the ECM (extracellular matrix). These growth factors provide a mechanism for induction of neovascularization in normal and pathological situations.

Heparanase may thus facilitate not only tumor cell invasion and metastasis but also tumor angiogenesis, both critical steps in tumor progression.

Specific inhibitors of the heparanase enzyme prevent release and activation of growth factors stored by heparan sulphate as well as disruption of the ECM, and are regarded as a very promising approach to develop anticancer drugs.

So, one of possible therapeutic approaches for an antiangiogenic drug is the development of a potent and selective heparanase inhibitor.

For a discussion of angiogenesis, reference may be made to WO 01/55221, in the name of the present applicant.

Another important involvement of heparanase is both inflammation and autoimmunity. In fact, heparanase activity correlates also with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulphate by heparanase activity. The enzyme is released from intracellular compartments (i.e. lysosomes, specific granules) in response to various activation signals, suggesting its regulated involvement and presence in inflammatory sites and autoimmune lesions. Treatment of experimental animals with heparanase inhibitors (i.e., non-anticoagulant species of low molecular weight heparin—LMWH) markedly reduced the incidence of experimental autoimmune encephalomyelitis (EAE), adjuvant arthritis and graft rejection in experimental animals, indicating that heparanase inhibitors may be applied to inhibit autoimmune and inflammatory disease.

Heparin

Heparin is a heterogeneous mixture of naturally occurring polysaccharides of various lengths and various degrees of sulphation which possesses anticoagulant activity and is secreted by the connective tissue mast cells present in the liver (from which it was first isolated), in the muscles, lungs, thymus and spleen.

In addition to the regular sequence, a sequence corresponding to the active site for antithrombin activity has been identified in heparin.

The antitumor and antimetastatic activity of heparin and its derivatives is due to its ability to inhibit heparanase, to block growth factors and to regulate angiogenesis.

Heparan Sulphates (HS)

Heparan sulphates (HS) are ubiquitous protein ligands. The proteins bind to the HS chains for a variety of actions from simple immobilisation or protection against the proteolytic degradation action to specific modulations of biological activities, such as angiogenesis.

The carbohydrate skeleton, in both heparin and the heparan sulphates (HS), consists in an alternation of D-glucosamine (GlcN) and hexuronic acids (GlCA or IdoA).

In heparin, the GlcN residues are mainly N-sulphated, whereas in HS they are both N-sulphated and N-acetylated, with a small amount of unsubstituted $NH_2$ groups.

HS is also on average less O-sulphated than heparin.

The use of heparin in the treatment of angiogenesis disorders, such as tumours, particularly metastases, is substantially limited by the anticoagulant activity of heparin.

Chemical modifications have been made to heparin so as to reduce its anticoagulant capacity, at the same time preserving its antitumor properties.

The opening of a unit of glucuronic acid in the antithrombin site reduces the affinity of heparin for antithrombin: in this way, heparins can be used with reduced anticoagulant effects, but still retaining antiangiogenic properties.

Heparanases

Heparanases are enzymes belonging to a family of endoglycosidases (an endo-□-D-glucuronidase) that hydrolyse the internal glycoside bonds of the chains of heparan sulphates (HS) and heparin.

These endoglycosidases are involved in the proliferation of tumour cells, in metastases and in the neovascularisation of tumours. These enzymes are biological targets for antiangiogenic activity. In the scientific literature there are a large number of structure/activity correlation studies (see, for example, Lapierre F. et al., *Glycobiology*, vol. 6, (3), 355-366, 1996). Though many aspects have still to be clarified, studies have been reported regarding the inhibition of heparanases by heparin and its derivatives, using specific tests which have led to the emergence of considerations of a structural type which may serve as guides for obtaining new, more selective derivatives.

In the above-mentioned work of Lapierre et al., heparin derivatives are described as obtained by 2-O desulphation or by "glycol split" (oxidation with periodate and subsequent reduction with sodium borohydride). These derivatives, defined here as "2-O-desulphated heparin" and "RO-heparin", respectively, have partly maintained the antiangiogenic activity of heparin as assessed by means of the CAM test in the presence of corticosteroids (ibid. page 360).

N-acyl heparin derivatives, which are closer mimics of heparan sulphate than heparin, have been reported to inhibit heparanase only somewhat less than N-sulphate derivatives. (Irimira T., *Biochemistry* 1986, 25, 5322-5328; Ishai-Michaeli R., et al, *Biochemistry* 1992, 31, 2080-2088).

Heparins and FGF

FGFs regulate multiple physiological processes such as cell growth and differentiation, but also functions involved in pathological processes such as tumour angiogenesis.

FGFs are growth factors (a family of more than 10 polypeptides, of which the acid (FGF-1) and basic FGFs (FGF-2) are the ones which have been most studied, which require a polysaccharide cofactor, heparin or HS, to bind to the FGF receptor (FGFR) and activate it.

Though the precise mechanism whereby heparin and HS activate FGFs is unknown, it is known, however, that heparin/FGF/FGFR form a "trimolecular" or "ternary" complex.

One mechanism postulated is that heparin and HS induce so-called sandwich dimerisation of FGF, and the latter, thus dimerised, forms a stable complex with FGFR.

Antimetastatic Activity of Heparin derivatives

The ability of a primary tumour to generate metastatic cells is perhaps the main problem facing anticancer therapy.

Heparin derivatives with a substantial ability to block heparanase seem to be equally capable of inhibiting angiogenesis both in primary tumours and in metastases.

In addition, the inhibition of heparanase reduces the migration ability of tumour cells from the primary tumour to other organs.

The antimetastatic activity in animal models has been found to correlate with the heparanase-inhibiting ability of heparin and heparin derivatives (Bitan M. et al, *Isr. J. Med. Sci.* 1995, 31, 106-108) as well as other sulphated polysaccharides (Miao, H. Q. et al, *Int. J. Cancer* 1999, 83, 424-431, and references therein). Studies on the molecular-weight dependence of the antimetastatic activity indicated that also very low-MW heparins (Sciumbata, T., et al, *Invasion Metastasis* 1996, 16, 132-143) and oligosaccharide polysulphates (Parish, C. R., et al, *Cancer Res.* 1999, 59, 3433-3441) retain significant antimetastatic activity. Although in general removal of N-sulphate groups (N-desulphation) decreases the antimetastatic potential of heparins, this activity is partially restored upon N-acylation (N-acetylation, N-hexanoylation (Bitan M., 1995), and N-succinylation (Sciumbata, T., 1996) of resulting free $NH_2$ groups. The antimetastatic activity of heparins was found to be inversely correlated to their degrees of O-sulphation. (Bitan M., 1995). However, selective 2-O-desulphation of iduronic acid residues did not involve a strong reduction of the antimetastatic activity of heparin (Lapierre, F., *Glycobiology* 1996, 6, 355-366).

In general, both the heparanase-inhibiting and the antimetastatic activity of heparins and other sulphated polysaccharides decrease with decreasing molecular weight and degree of sulphation (Bitan M., 1995; Parish, C. R., 1999). However, these activities also depend on the carbohydrate backbone of the polysaccharide (type of residues and position of glycosydic linkages) (Parish, C. R., 1999). Since the tridimensional structure of the active site of heparanase is not yet known, it is difficult to predict which polysaccharide backbones and sulphation patterns most effectively inhibit the enzyme.

On the basis of the present knowledge, the structural requirements of heparin-like molecules that favour the angiogenesis-inhibiting action can be grouped in two categories on the basis of the target one intends to block:

a) inhibition of heparanase: although this enzyme recognizes and cleaves heparin and HS sequences of at least eight monosaccharide units containing N-acyl-glucosamine-glucuronic acid (or N-sulphated glucosamine residues see, for example, D. Sandback-Pikas et al. *J. Biol. Chem.*, 273, 18777-18780 (1998) and references cited), its inhibition can be efficiently accomplished by heparin fragments longer than tetradecasaccharide (Bitan M., 1995) or by extensively sulphated, shorter oligosaccharides, such as maltohexaose sulphate (MHS) and phosphomannopentaose sulphate (PI-88) (Parish, C. R., 1999). However, both long heparin fragments and heavily sulphated oligosaccharides are anticoagulant, a property that should be avoided for potential antimetastatic drugs;

b) inhibition of angiogenic growth factors (fibroblast type: FGF-1 and FGF-2; vascular endothelium type: VEGF; vascular permeability type: VPF): to this end the heparin-like compounds preferably have sequences at least five monosaccharide units long, containing 2-sulphated iduronic acid and glucosamine N,6-sulphated (see, for example, M. Maccarana et al. *J. Biol. Chem.*, 268, 23989-23905 (1993)).

The literature discloses small peptides (5-13 amino acids) with antiangiogenic activity (U.S. Pat. No. 5,399,667 of the University of Washington) which act by binding to a thrombospondin receptor, or longer peptides (50 amino acids approx.).

Modified platelet factors are known—(EP 0 589 719, Lilly), capable of inhibiting endothelial proliferation, with $IC_{50}$=7 nM.

Oligosaccharide fragments with antiangiogenic activity have also been amply described: it has been found, in fact, that by varying the carbohydrate sequence the interaction selectivity can be increased.

In addition, heparin can be used as a vehicle for substances which are themselves antiangiogenic, such as some steroids, exploiting the affinity of heparin for vascular endothelial cells; see, for example, WO 93/18793 of the University of Texas and Imperial Cancer Research Technology, where heparins are claimed with acid-labile linkers, such as adipic acid hydrazine, bound to cortisol. The antiangiogenic effect of the conjugated molecules is greater than that of the unconjugated molecules, even when administered simultaneously.

In *Biochim Biophys. Acta* (1996), 1310, 86-96, heparins bound to steroids (e.g. cortisol) are described with a hydrazone group in C-20 that present greater antiangiogenic activity than the two unconconjugated molecules.

EP 0 246 654 by Daiichi Sc. describes sulphated polysaccharides with antiangiogenic activity with Phase II studies. EP 0 394 971 by Pharmacia & Upjohn—Harvard Coll. describes hexa-saccharides—heparin fragments—with low sulphation, capable of inhibiting the growth of endothelial cells and angiogenesis stimulated by FGF-1. EP 0 618 234 by Alfa Wasserman describes a method for preparing semisynthetic glycosaminoglycans with a heparin or heparan structure bearing a nucleophilic group. WO 95/05182 by Glycomed describes various sulphated oligosaccharides with anticoagulant, antiangiogenic and anti-inflammatory activity. U.S. Pat. No. 5,808,021 by Glycomed describes a method for preparing substantially non-depolymerised 2-O, 3-O desulphated heparin with a desulphation percentage in positions 2- of the iduronic acid (I, 2-O) and in position 3 of the glucosamine unit (A, 3-O) ranging from approximately 99 to approximately 75% of the original percentage. This method envisages desulphation conducted in the presence of a cation of a bivalent metal, exemplified by calcium or copper, followed by lyophilisation of the product obtained. The desulphated heparins have antiangiogenic activity. EP 0 251 134, Yeda Res & Dev Co Ltd et al, discloses the use of subcoagulant dosages of heparin or its derivatives for preventing allograft rejection and treating autoimmune diseases. The activity of heparin is given by inhibition of heparanase. WO 88/05301, Univ. Australian Nat., discloses antimetastatic and/or antiinflammatory compositions containing a sulphated polysaccharide, which is heparanase inhibitor. Heparin, fucoidan, pentosan sulphate, dextran sulphate are provided. WO 92/01003, Univ. Texas System, discloses the use of a heparin derivative, which is devoid of anticoagulation activity, as heparanase inhibitor. These derivatives have sulphamino or O-sulphate groups, M.W. 1000-15000 and each terminal monomeric unit is a monomeric repeating unit with a terminal O atom bound to a blocking group. WO 94/14851 and WO 96/06867, Glycomed, provide 2-O, 3-O-de-sulphated mucosal heparin, or fragments thereof, being at least 96.7% de-sulphated at the 2-O position and ate least 75% desulphated at the 3-O position useful as non-anticoagulant heparanase inhibitors. WO 95/09637 and WO 96/09828, Glycomed, discloses highly sulphated maltooligosaccharide compounds with heparin like properties. WO 95/30424, Glycomed, provides 6-O-desulphated heparin or fragments thereof with heparanase inhibiting activity. WO 96/33726, Univ. Australian Nat., discloses sulphated oligosaccharides as heparan mimetics having heparanase inhibiting activity. WO 01/35967, Knoll A G, provides a method for treating cardiac insufficiency and related conditions by administering an heparanase inhibitor, among which, heparin which has partly reduced COOH groups, or is at least partly N-desulphated and N-acetylated or is at least partly N,O-desulphated and N-resulphated or is O-acetylated is mentioned.

The aim of the invention described herein is to find optimal glycosaminoglycan structures for generating antiangiogenic activity based on heparanase inhibition and/or FGF growth factor inhibition mechanisms. An additional aim of the invention described herein is to provide a medicament with antiangiogenic activity which is essentially devoid of the typical side effects of heparin derivatives, such as, for example, anticoagulant activity.

WO 01/55221, in the name of the applicant, discloses glycosaminoglycans, particularly a desulphated heparin, with a desulphation degree not greater than 60% of the total uronic units. These derivatives are provided with antiangiogenic activity and are devoid of anticoagulant activity. Said compounds exert their antiangiogenic activity based on the inhibition of FGF. No activity was foreseen for inhibition of heparanase.

In quite general terms, WO 01/55221 also provides a modified heparin, containing glycosamine residues with different degrees of N-desulphation and optional subsequent total or partial acetylation. The general teaching of said reference does not explicitly describe the N-desulphation and optional subsequent total or partial acetylation steps.

Each data point is the average of triplicate wells and the variation did not exceed 10% of the mean.

Figure 10:
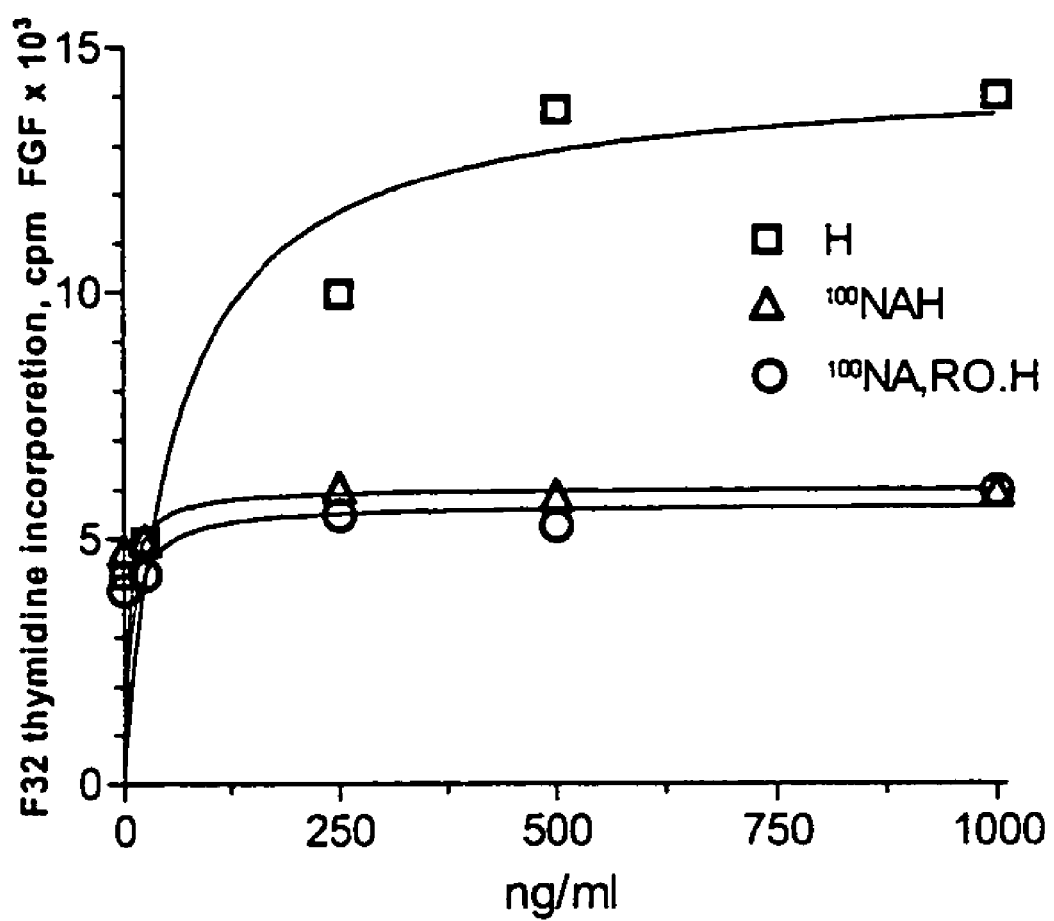

FIG. 10. N-acetyl heparin and its corresponding glycol-split derivative fail to stimulate the mitogenic activity of FGF-2. BaF3 (F32) lymphoid cells were plated into 96-well microtiter plates in the presence of 2.5 ng/ml FGF-2 and increasing concentrations of heparin (H-1), 100% N-acetylated heparin (100NAH), or the corresponding 25% glycol-split, 100% N-acetylated heparin (100NA, RO.H). After 48 h, 3H-thymidine was added (1 μCi/well) and the amount of incorporated thymidine was determined as described in "Experimental Procedures". Each data point is the average of triplicate wells and the variation did not exceed 10%.

SUMMARY OF THE INVENTION

It has now been found that on subjecting a glycosaminoglycan, such as a heparin-like glycosaminoglycan, heparin or modified heparin, containing glucosamine residues with different degrees of N-desulphation and optional subsequent total or partial N-acylation (preferably N-acetylation), to controlled 2-O-desulphation treatment of the iduronic units up to a degree of desulphation not greater than 60% of the total uronic units, the growth-factor-mediated angiogenic properties are maintained.

Surprisingly, heparin 2-O-desulphated disclosed in the above mentioned WO 01/55221 are also inhibitors of heparanes. This property was found to be further enhanced upon glycol splitting of non-sulphated uronic acid residues. Glycol-splitting, a chemical modification leading to a dramatic loss of anticoagulant activity (Casu B., et al, *Arzneim Forsch (Drug Res.)* 1986, 36, 637-642) was also found to dramatically enhance the heparanase-inhibiting properties of partially N-acetylated heparins obtained through 50% N-desulphation followed by N-acetylation of the resulting free amino groups and of the 2-O-desulphated compounds.

The desulphation carried out in the conditions described in the present invention also produces the formation of iduronic units with an oxyranic ring in position 2,3. The opening of the oxyranic ring in the conditions described in the present invention gives rise to L-iduronic or L-galacturonic units.

It is an object of the invention described herein the use of said glycosaminoglycan derivatives for the preparation of a medicament having heparanase and/or FGF growth factor inhibiting activity.

According to the present invention, said glycosaminoglycan derivative is preferably a heparin-like glycosaminoglycan. Still according to the present invention, said glycosaminoglycan derivative is a modified heparin, containing glycosamine residues with different degrees of N-desulphation and optional subsequent total or partial N-acetylation.

In one particular embodiment, the invention described herein refers to a formula (I) compound where the U ring may have the following meanings:

X and X', which can be the same or different, are an aldehyde group or the —$CH_2$-D group, where D is hydroxyl or an amino acid, a peptide or a residue of a carbohydrate or oligosaccharide;

R and $R_1$, which can be the same or different, are an $SO_3$, a $C_1$-$C_8$ acyl residue, optionally bearing at least a further carboxy group; acetyl, hexanoyl, succinyl, pivaloyl are the preferred acyl residues;

n and m, which can be the same or different, may vary from 1 to 40; the sum of n+m ranges from 6 to 40; the m:n ratio ranges from 10:2 to 1:1;

The symbol ⌇ indicates that the units marked m and n are statistically distributed along the polysaccharide chain and are not necessarily in sequence.

Examples of $C_1$-$C_8$ acyl residue, optionally bearing at least a further carboxy group are acetyl, propionyl, butyryl, pentanoyl, hexanoyl, heptanoyl, and all the possible isomers, oxalyl, malonyl, succinyl, pivaloyl, glutaroyl; acetyl, hexanoyl, pivaloyl are the preferred acyl residues.

When R or $R_1$ are N-acyl groups, they preferentially range from 40 to 60% of the sum R+$R_1$. Preferably, m is greater than or equal to n. Preferably n ranges from 40 to 60% of the sum m+n.

The compounds of formula (I) above, wherein R and $R_1$ are $C_1$ or $C_3$-$C_8$ acyl residue are new.

The compounds which are the subject matter of the invention described herein, are characterized by a high power of inhibiting heparanase with interesting antiangiogenic properties, and are therefore useful as active ingredients for the preparation of medicaments for the treatment of pathologies gaining benefit from the inhibition of the heparanase, pathologies based on abnormal angiogenesis, and particularly for the treatment of metastases.

The compounds according to the present invention also inhibit FGFs.

Advantageously, the compounds according to the present invention show reduced, if not non-existent anticoagulant properties, thus avoiding or reducing the side effects typical of the heparins. A further advantage stems from the fact that the compounds according to the invention can be characterised with instrumental analytical techniques, such as NMR spectroscopy, thus allowing process control which is absolutely desirable from the industrial point of view.

Also in the case of modified heparins, molecular weight (MW) has a very important function when making angiogenesis inhibitors. It is well known, in fact, that a reduction in molecular weight (MW) up to values corresponding to pentasaccharide units does not lead to a loss of antiangiogenic activity. On the other hand, it has been established that, whereas beyond a certain length the heparin chains favour rather than inhibit activation of FGF, they are even better inhibitors of heparanase than shorter chains. However, the optimal chain length for inhibition of heparanase depends on the structure of the inhibitor (carbohydrate backbone, positional linkages, sulphation pattern) and should be established for any new type of potential inhibitors.

DETAILED DESCRIPTION OF THE INVENTION

The compounds according to the present invention containing glycosamine residues with different degrees of N-desulphation and optional subsequent total or partial acetylation are herein specifically disclosed and claimed as new compounds.

What is meant by desulphation degree is the percentage of non-sulphated iduronic acids in relation to total uronic acids originally present in the starting heparin. One initial preferred range for the desulphation percentage is from approximately 40 to approximately 60%.

Among the formula (I) compounds, a first preferred compound is a heparin partially 2-O-desulphated with a molecular weight (MW) of 11200, a polydispersion index D of 1.3, a desulphation degree of 1.99 (expressed as the $SO_3$—:$COO$— molar ratio), a percentage of modified uronic acids compared to total uronic acids of approximately 50%. Said compound (hereinafter also called ST1514) is comprised in formula (I) where, among the other corresponding definitions, m:n=1:1 and the units marked m and n are distributed along the polysaccharide chain in a regular, alternating manner.

A second preferred compound is an LMW heparin partially 2-O-desulphated with a molecular weight (MW) of 3050, a polydispersion index of 2.2, a desulphation degree of 1.99 (expressed as the $SO_3$—:$COO$— molar ratio), a percentage of modified uronic acids compared to total uronic acids of approximately 50%. Said compound (hereinafter also called ST2010) is comprised in formula (I) where, among the other corresponding definitions, m:n=1:1 and the units marked m and n are distributed along

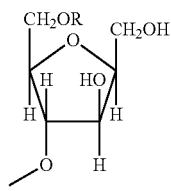

the polysaccharide chain in a regular, alternating manner. This compound is obtained by nitrous acid depolymerization of ST1514, followed by reduction of aldehyde groups, therefore most of its reducing end residues are anhydromannose residues:

A third preferred compound is an LMW heparin partially 2-O-desulphated with a molecular weight of Mn=5800, Mw=7520, a polydispersion index of 1.294, a percentage of modified uronic acids compared to total uronic acids of approximately 50%. Said compound (hereinafter also called Sm 184) is comprised in formula (I) where, among the other corresponding definitions, m:n=1:1 and the units marked m and n are distributed along the polysaccharide chain in a regular, alternating manner. This compound is obtained by nitrous acid depolymerization of ST1514, followed by reduction of aldehyde groups, therefore most of its reducing end residues are anhydromannose residues.

A fourth preferred compound is a partially N-desulphated and N-reacetylated heparin with a molecular weight (MW) of 11200, a polydispersion index of 1.3, a desulphation degree of 1.6 (expressed as the $SO_3$—:$COO$— molar ratio), a percentage of modified uronic acids compared to total uronic acids of approximately 30%. Said compound (hereinafter also called ST1518) is comprised in formula (I) where, among the other corresponding definitions, the 50% of the sum of R and $R_1$ is N-acetyl.

A fifth preferred compound is an LMW partially N-desulphated and N-reacetylated heparin with a molecular weight of Mn=4780, Mw=10000, a polydispersion index of 2.092, a percentage of modified uronic acids compared to total uronic acids of approximately 30%. Said compound (hereinafter also called ST2168) is comprised in formula (I) where, among the other corresponding definitions, the 50% of the sum of R and $R_1$ is N-acetyl.

A sixth preferred compound is a partially N-desulphated and N-reacetylated heparin with a molecular weight of Mn=10890, Mw=22370, a polydispersion index of 2.054. Said compound (hereinafter also called ST2037) is comprised in formula (I) where, among the other corresponding definitions, the 27% of the sum of R and $R_1$ is N-acetyl.

A seventh preferred compound is a partially N-desulphated and N-reacetylated heparin with a molecular weight of Mn=10210, Mw=21270, a polydispersion index of 2.083. Said compound (hereinafter also called ST2038) is comprised in formula (I) where, among the other corresponding definitions, the 39% of the sum of R and $R_1$ is N-acetyl.

An eighth preferred compound is a partially N-desulphated and N-reacetylated heparin with a molecular weight of Mn=11070, Mw=22000, a polydispersion index of 1.987. Said compound (hereinafter also called ST2041) is comprised in formula (I) where, among the other corresponding definitions, the 64% of the sum of R and $R_1$ is N-acetyl.

A ninth preferred compound is a partially N-desulphated and N-reacetylated heparin, a percentage of modified uronic acids compared to total uronic acids of approximately 30%. Said compound is comprised in formula (I) where, among the other corresponding definitions, the 27% of the sum of R and $R_1$ is N-acetyl (ST2185).

A tenth preferred compound is a partially N-desulphated and N-reacetylated heparin, a percentage of modified uronic acids compared to total uronic acids of approximately 30%. Said compound (hereinafter also called ST2186) is comprised in formula (I) where, among the other corresponding definitions, the 39% of the sum of R and $R_1$ is N-acetyl.

A eleventh preferred compound is a partially N-desulphated and N-reacetylated heparin, a percentage of modified uronic acids compared to total uronic acids of approximately 30%. Said compound (hereinafter also called ST2187) is comprised in formula (I) where, among the other corresponding definitions, the 64% of the sum of R and $R_1$ is N-acetyl.

A twelfth preferred compound is a partially 2-O-desulphated heparin with a molecular weight (MW) of 12900 D, a polydispersion index D of 1.5, a desulphation degree of 1.9 (expressed as $SO_3$—:COO— molar ratio), percentage of modified uronic acids compared to total uronic acids: 5% epoxide groups, 29% oxidated and reduced uronic residues. Said compound (hereinafter also called ST1513) is comprised in formula (I) where, among the other corresponding definitions, m:n=1:1 and the units marked m and n are distributed along the polysaccharide chain in a regular, alternating manner.

A thirteenth preferred compound is a partially 2-O-desulphated heparin with a molecular weight (MW) of 9200 D, a polydispersion index D of 1.5, percentage of modified uronic acids compared to total uronic acids: 11% epoxide groups, 27.5% oxidated and reduced uronic residues. Said compound (hereinafter also called ST1515) is comprised in formula (I) where, among the other corresponding definitions, m:n=1:1 and the units marked m and n are distributed along the polysaccharide chain in a regular, alternating manner.

A fourteenth preferred compound is a partially 2-O-desulphated heparin with a molecular weight (MW) of 11000 D, a polydispersion index D of 1.5, a desulphation degree of 1.93 (expressed as $SO_3$—:COO— molar ratio), a percentage of modified uronic acids compared to total uronic acids: 5% epoxide groups, 29% oxidated and reduced uronic residues.

The preparation of compound ST1514, ST1513, ST1516 and ST1515 are specifically disclosed in WO 01/55221.

The partially 2-O-desulphated derivatives according to the invention described herein are prepared as disclosed in the above mentioned WO 01/55221.

As far as the N-desulphated and optionally N-acetylated glycosaminoglycans according to the present invention, they can be prepared by means of a process, enabling also the preparation of the 2-O-partially desulphated heparins, comprising:

a) N-desulphation by solvolytic hydrolysis of sulphamino residues in DMSO:$H_2O$ 95:5 v:v at ambient temperature for a time ranging from 0.5 to 8 h, and even more preferably for approximately 2 h, to give the total or partial elimination of sulphate groups at position 2 of the glucosamine residues;

b) N-acylation of said totally or partially desulphated groups at position 2 of the glucosamine residues by treatment in alkaline aqueous solution (pH 8-9) with an acylating agent, such as acyl anhydrides, to give totally or partially acylated groups at position 2 of the glucosamine residues; then submitting the obtained compounds to steps c), d) or e) and f-g) below, or alternatively directly to step f) below;

c) basic treatment at a temperature ranging from ambient temperature to approximately 100° C., preferably from 50 to 70° C., and even more preferably at approximately 65° C., which leads to the elimination of a controlled percentage of sulphate groups in position 2 of the iduronic acid and to the formation of epoxide groups; and, if desired d) opening of said epoxide ring at approximately pH 7, at a temperature ranging from approximately 50° C. to approximately 100° C., preferably at approximately 70° C., to yield residues of galacturonic acid; or, alternatively e) opening of said epoxide ring at a temperature ranging from approximately 0° C. to 30° C., preferably at approximately 25° C., to yield residues of iduronic acid; and, if desired f) oxidation of the diols with sodium periodate, to yield the opening of the glycoside ring and the formation of two aldehyde groups per modified residue; and, if desired;

g) reduction of said aldehyde groups to primary alcohol and, if desired, transformation of the D group to a group other than hydroxyl, as envisaged in the different meanings assigned in formula (I);

h) optional acid hydrolysis of compounds obtained in step g) to obtain oligosaccharides corresponding to the regular sequences, preferably by deamination with nitrous acid. This reaction, which is usually applied to obtain LMW heparin by cleaving the linkage between N-sulphate glucosamine residues and the next uronic acid, leads to a LMW compound having at the non reducing end a residue consisting of an uronic acid and at the reducing end a residue of anhydro mannose, this latter can be further modified to anhydromannitol by reduction with borohydride. The obtained LMW compounds contain at least one residue of glycol-split iduronic acid; or alternatively i) submitting the products obtained in step g) to partial enzymatic hydrolysis with an enzyme selected from the group consisting of lyase, heparinase, heparitinase, or equivalent of to yield oligosaccharides, preferably tetra- or octa-saccharides, with the non-reducing terminal residue consisting of unsaturated iduronic acid, the reducing residue consisting of an N-sulphoglucosamine and containing at least one residue of open iduronic acid.

i) optionally the compound obtained in step c) or the product obtained in step d) is treated by partial enzyme hydrolysis; and, if desired j) subjection of the products obtained in one of steps b), c), and f) to partial 6-O-desulphation; or, alternatively, k) subjection of the starting heparin partially or totally 6-desulphated to steps b), c) and f).

The 2-O-desulphated derivatives according to the present invention are obtained with the process above disclosed by omitting steps a) and b).

The process according to the present invention is also illustrated by the schemes below:

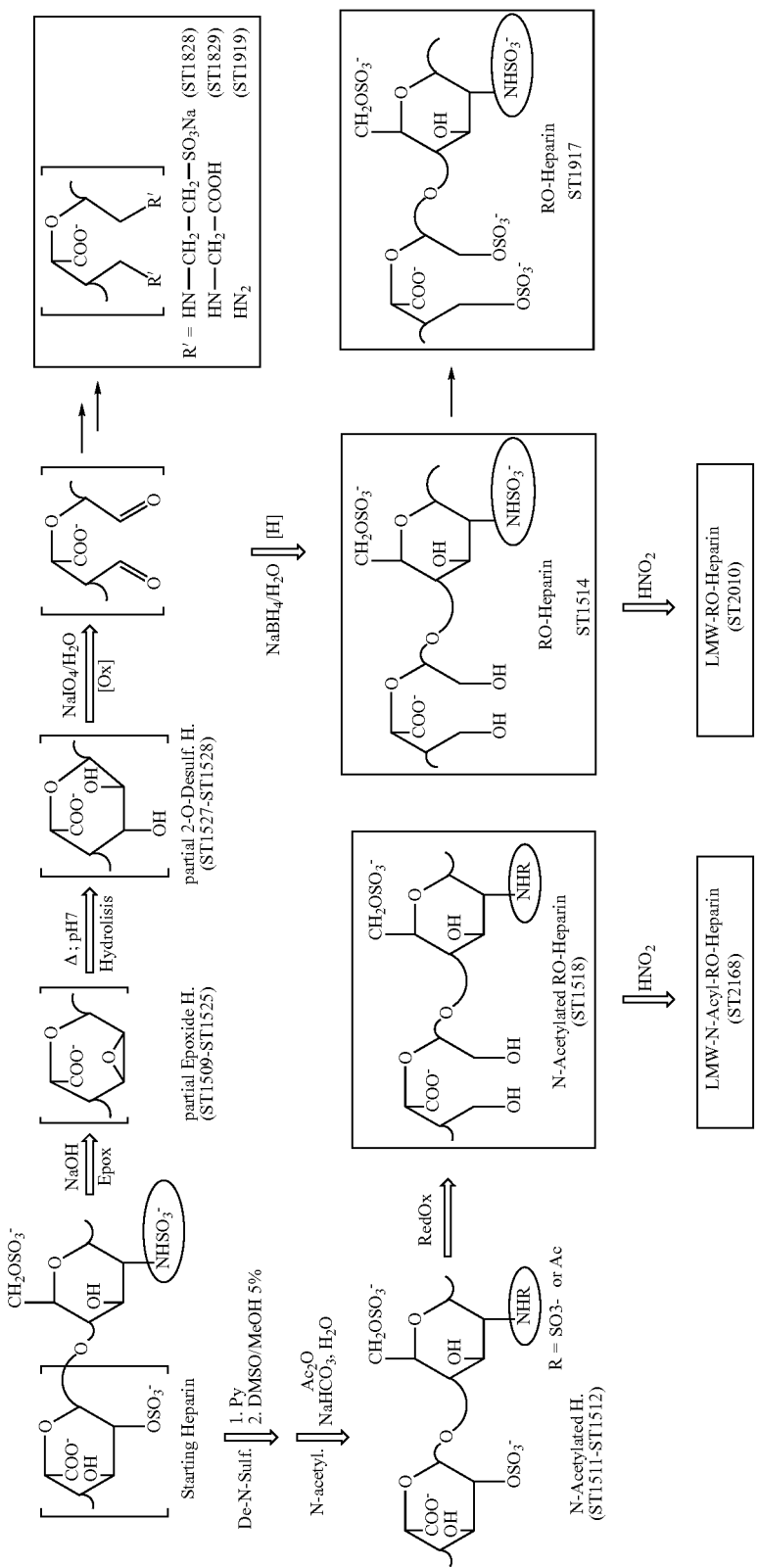

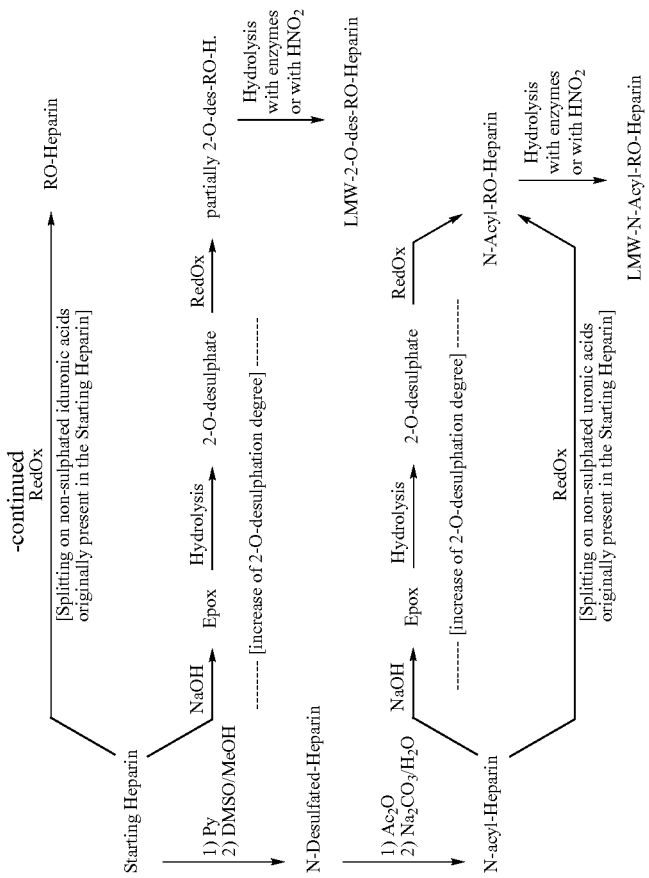

According to the invention described herein, the preferred compound are:

heparin partially 2-O-desulphated, obtainable by the process described above, where steps a) and b) are omitted, step c) is conducted for 45 min at 60° C., and step d) at 70° C. at pH 7, and having a molecular weight (MW) of 11200, a polydispersion index D of 1.3, a desulphation degree of 1.99 (expressed as the $SO_3{-}$:$COO{-}$ molar ratio), percentage of modified uronic acid compared to total uronic acid of approximately 50% (hereinafter also called ST1514);

LMW heparin partially 2-O-desulphated, obtainable by the process described above, where steps a) and b) are omitted, step c) is conducted for 45 min at 60° C. and step d) at 70° C. at pH 7, followed by step f) g) and h) conducted by deamination and having a molecular weight (MW) of 3050, a polydispersion index D of 2.2, a desulphation degree of 1.99 (expressed as the $SO_3{-}$:$COO{-}$ molar ratio), a percentage of modified uronic acid compared to total uronic acid of approximately 50% (hereinafter also called S2010);

LMW heparin partially 2-O-desulphated, obtainable by the process described above, where steps a) and b) are omitted, step c) is conducted for 45 min at 60° C. and step d) at 70° C. at pH 7, followed by step f) g) and h) conducted by deamination and having a molecular weight $Mn=5800$, $Mw=7520$, a polydispersion index D of 1.294, a percentage of modified uronic acid compared to total uronic acid of approximately 50% (hereinafter also called ST2184);

heparin N-acetyl (50%), obtainable by the process described above, where step a) is conducted for 2 h at room temperature and step b) for 2 h at 4° C., steps c), d), e) are omitted, step f) is conducted at 4° C. for one night, step g) for 3 h at room temperature and having a molecular weight (MW) of 11200, a polydispersion index D of 1.3, a desulphation degree of 1.6 (expressed as the $SO_3{-}$:$COO{-}$ molar ratio), percentage of modified uronic acids compared to total uronic acids of approximately 30% (hereinafter also called ST1518).

LMW heparin N-acetyl (50%), obtainable by the process described above, where step a) is conducted for 2 h at room temperature and step b) for 2 h at 4° C., steps c), d), e) are omitted, step f) is conducted at 4° C. for one night, step g) for 3 h at room temperature, step h) is conducted by nitrous acid deamination at 4° C. for 17 min, followed by reduction of aldehyde groups with borohydride at room temperature for 3 h, and having a molecular weight of $Mw=4780$, $Mn=10000$, a polydispersion index D of 2.092, a percentage of modified uronic acids compared to total uronic acids of approximately 30% (hereinafter also called ST2168).

heparin N-acetyl (27%), obtainable by the process described above, where step a) is conducted for 2 h at room temperature and step b) for 2 h at 4° C., steps c), d), e), f), g), h) are omitted, and having a molecular weight of $Mn=10890$, $Mw=22370$, a polydispersion index D of 2.054 (hereinafter also called ST2037).

heparin N-acetyl (39%), obtainable by the process described above, where step a) is conducted for 2 h at room temperature and step b) for 2 h at 4° C., steps c), d), e), f), g), h) are omitted, and having a molecular weight of $Mn=10210$, $Mw=21270$, a polydispersion index D of 2.083 (hereinafter also called ST2038).

heparin N-acetyl (64%), obtainable by the process described above, where step a) is conducted for 2 h at room temperature and step b) for 2 h at 4° C., steps c), d), e), f), g), h) are omitted, and having a molecular weight of $Mn=11070$, $Mw=22000$, a polydispersion index D of 1.987 (hereinafter also called ST2041).

heparin N-acetyl (27%), obtainable by the process described above, where step a) is conducted for 2 h at room temperature and step b) for 2 h at 4° C., steps c), d), e), f), g), h) are omitted, and having a percentage of modified uronic acids compared to total uronic acids of approximately 30% (hereinafter also called ST2185).

heparin N-acetyl (39%), obtainable by the process described above, where step a) is conducted for 2 h at room temperature and step b) for 2 h at 4° C., steps c), d), e), f), g), h) are omitted, and having a percentage of modified uronic acids compared to total uronic acids of approximately 30% (hereinafter also called ST2186).

heparin N-acetyl (64%), obtainable by the process described above, where step a) is conducted for 2 h at room temperature and step b) for 2 h at 4° C., steps c), d), e), f), g), h) are omitted, and having a percentage of modified uronic acids compared to total uronic acids of approximately 30% (hereinafter also called ST2187).

The preparation of compounds ST1514, ST1513, ST1516 and ST1515 are specifically disclosed in WO 01/55221.

The molecular weights are determined by HPLC-GPC (high performance liquid chromatography—gel permeation chromatography). The desulphation degree is determined by conductimetry and the percentage of modified uronic acids by $^{13}$C-NMR.

MW is the molecular weight, and D is the polydispersion index expressed as MW/Mn.

According to the invention described herein, the starting products are glycosaminoglycans of various origins, preferably naturally occurring heparins. It is also possible to use chemically modified heparins with a percentage content of N,6 disulphate ranging from 0 to 100%. Starting from products with a different 6-O-sulphated glucosamine content, it is possible to modulate the length of the regular sequences between one open iduronic acid and another. The glycosaminoglycans according to the invention that present opening of the glycoside ring are conventionally called RO derivatives by those skilled in the field, meaning by this that the glycoside ring has been opened by means of an oxidation action, followed by a reduction (Reduction-Oxidation—RO). This opening of the glycoside ring is also conventionally called "glycol split", so-called because of the formation of the two primary hydroxy present on the open ring. The compounds referred to herein will also be called "RO" or "Glycol Split" derivatives.

In a further embodiment of the invention described herein, the aldehydes and primary hydroxy derived from the opening reaction described above ("glycol split") also lend themselves to the subsequent functionalisation. Therefore, formula (I) compounds may also bear equal or different groups, as defined above for X and X', on the primary hydroxy deriving from glycol split, for example, oligosaccharide or peptide groups, ranging from a single saccharide or amino acid to more than one unit of length, preferably 2 or 3 units.

Formula (I) compounds where X and X are $-CH_2OH$ can also be used as vehicles for other types of drugs, by means of suitable binding with the heparin portion which is capable of providing a stable bond in normal conditions of manufacture and storage of a formulated drug, which, however, releases the transported drug in the body, preferably in the vicinity of the target organ. Examples of drugs that can be transported are steroidal and non-steroidal anti-inflammatory drugs, corticosteroids, and other drugs with an antimetastatic action, in which case there will be an advantageous enhancement of the antimetastatic effect as a result of the sum of the separate intrinsic activities of the compounds according to the invention and the antimetastatic agent bound thereto, with the related advantages of a greater target selectivity and lower systemic toxicity. Examples of these drugs are the metalloproteinase inhibitors. Other drugs which can be usefully transported are those that act at the endothelial level. Formula (I) compounds where X and X' are other than hydroxy or aldehyde can also be used as vehicles for drugs, in which case the X and X' groups will act as "spacers" between the transported molecule, that is to say the glycosaminoglycan of the present invention and the molecule acting as the vehicle, in those cases where this may be desirable for reasons of pharmacokinetics or pharmacodynamics.

In the case of compounds according to the invention deriving from heparin, these are prepared starting from heparin as such by means of N-desulphation followed by N-acylation using techniques known to the technical experts in the field. For example, the N-desulphation is conducted by solvolysis in DMSO:$H_2O$ solution 95:5 v:v at room temperature for time ranging from 0.5 to 8 h followed by N-acylation in alkaline condition with, for example, acylanhydrides (i.e., acetyl, hexanoyl, succinyl, pivaloyl).

The following 2-O-desulphation is conducted in the presence of alkaline agents, such as sodium hydroxide, at temperatures ranging from ambient temperature to 100° C., preferably from 50 to 70° C., for example at 60° C., for a sufficiently long period to obtain the desired 2-O-desulphation. The 2-O-desulphation is controlled by acting on the process parameters, such as the concentrations of reactants, the temperature and the reaction times. One preferred example consists in maintaining constant concentrations of substrate (glycosaminoglycan) at 80 mg/ml and of NaOH at 1 M, a constant temperature of 60° C. and controlling the desulphation with a reaction time from 15 to 60 min. The expert in the field may vary the conditions, for example by raising the reaction temperature and shortening the reaction time, on the basis of normal trial and error in experimental practice and on the basis of his or her general knowledge of the subject.

The treatment with alkaline agents gives rise to an intermediate product characterised by the presence of an epoxide ring on the desulphated unit. In a thoroughly surprising manner, these intermediates have proved to be endowed with heparanase inhibiting properties similar to those of the formula (I) compounds. Therefore, a further object of the invention described herein is a derivative of partially 2-O-desulphated heparin, and therefore heparin with a reduced charge, particularly heparin not 2-O-desulphated more than 60%, characterised by an epoxide ring on the desulphation site. Said compounds characterised by an epoxide ring also belong to the whole scope covered by the present invention.

Subsequent to the formation of the epoxide ring, the latter is opened, again resorting to known techniques. The percentage of epoxide formed is calculated from the ratio between the areas of the $^{13}$C-NMR signals at approximately 55 ppm, characteristic of carbons 2 and 3 of the uronic acid ring containing the epoxide and the total number of anomeric signals (C1 of the glucosamine and uronic acid residues). If the opening is conducted hot, a galacturonic acid residue is obtained, whereas, if the opening of the epoxide ring is conducted cold, an iduronic acid residue is obtained. Preferred examples of compounds containing an epoxide ring are those obtainable by the process described above and having epoxidated uronic acid contents of 14% (hereinafter ST1509), 24% (hereinafter ST1525) and 30% (hereinafter ST1526), respectively.

The partially desulphated heparin is then subjected to "glycol-split" (RO for short), according to the process defined above and Smith degradation (SD for short).

Alternatively, formula (I) compounds can also be obtained without passing via the epoxide intermediate, that is to say by direct glycol split and subsequent Smith degradation.

The process described so far leads to formula (I) compounds in which the X and X' groups are both —$CH_2OH$.

For X and X' other than —$CH_2OH$, methods are available to the expert in the field for transforming the hydroxyl group with other groups envisaged in the definitions given above (see for example Scheme on page 26, compounds ST1828, ST1829, ST1917 and ST1919). For example, the conjugation with amino acids or peptides can be done by treating the intermediate aldehyde derived from the glycol-split reaction with a reductive amination reaction (Hoffmann J. et al. Carbohydrate Research, 117, 328-331 (1983)), which can be conducted in aqueous solvent and is compatible with maintenance of the heparin structure.

If desired, and this constitutes a further object of the invention described herein, the formula (I) compounds can be further degraded with acid agents in suitable pH conditions, e.g. at pH 4, to yield a mixture of oligosaccharides that maintain the antiangiogenic properties.

In the same way, objects of the present invention are the compounds obtained by one of the steps g), h), i) and j) of the process described above.

Objects of the invention described herein are pharmaceutical compositions containing as their active ingredient at least one formula (I) compound, alone or in combination with one or more formula (I) compounds, or, said formula (I) compound or compounds in combination with the N-acyl-desulphated heparins described above, e.g. the epoxidated intermediates; the latter can also be used alone as active ingredients in the pharmaceutical compositions. The active ingredient according to the present invention will be in a mixture with suitable vehicles and/or excipients commonly used in pharmaceutical technology, such as, for instance, those described in "Remington's Pharmaceutical Sciences Handbook", latest edition. The compositions according to the present invention will contain a therapeutically effective quantity of the active ingredient. The doses will be determined by the expert in the field, e.g. the clinician or primary care physician according to the type of disease to be treated and the patient's condition, or concomitantly with the administration of other active ingredients. By way of an example, doses ranging from 0.1 to 100 mg/kg may be indicated.

Examples of pharmaceutical compositions are those that can be administered orally or parenterally, intravenously, intramuscularly, subcutaneously, transdermally or in the form of nasal or oral sprays. Pharmaceutical compositions suitable for the purpose are tablets, hard or soft capsules, powders, solutions, suspensions, syrups, and solid forms for extemporary liquid preparations. Compositions for parenteral administration are, for example, all the intramuscular, intravenous and subcutaneous injectable forms as well as solutions, suspensions and emulsions. Liposome formulations should also be mentioned. The tablets also include forms for the controlled release of the active ingredient whether as oral administration forms, tablets coated with suitable layers, microencapsulated powders, complexes with cyclodextrins, depot forms, for example, subcutaneous forms, such as depot injections or implants.

The compounds according to the invention described herein possess anti-heparanase and antiangiogenic activity. This makes them suitable for the preparation of medicaments useful for the treatment of subjects, generally mammals, and particularly human subjects, suffering from altered angiogenesis or subjects who need a treatment inhibiting the heparanasic activity.

Examples of diseases treated with the medicament which is the object of the present invention are primary tumours, metastases, diabetic retinopathies, psoriasis, retrolenticular fibroplasia, restenosis after angioplasty, coronary by-pass, inflammation, arthritis, autoimmune diseases, allograft rejection, cardiovascular diseases, fibro-proliferative disease, diseases elicited by abnormal platelet aggregation, diseases elicited by smooth muscle proliferation, Goodpasture syndrome, acute glomerulonephritis, neonatal pulmonary hypertension, asthma, congestive heart failure, adult pulmonary hypertension, renal vascular hypertension, proliferative retinopathies, experimental autoimmune encephalomyelitis, multiple sclerosis, insulin dependent diabetes, inflammatory bowel disease, ulcerative colitis, Crohn's disease.

Advantageously, the compounds according to the present invention are substantially devoid of the side effects typical of heparin. In particular, the compounds according to the invention are substantially devoid of anticoagulant activity. By substantially devoid of such activity the expert in the field means no or only negligible activity from the point of view of clinical use.

The heparanase inhibiting activity was determined according to a method established by Vlodavsky's group (Bitan M. et al, 1995). The method is based on evaluation of the extent of fragmentation of the heparan sulphate chains of heparan sulphate proteoglycans (HSPG) caused by heparanase. Sulphate labelled extracellular matrix (ECM) is most commonly used as a source of HSPG. Sulphate labelled ECM is incubated with recombinant heparanase at pH 6.2 in the absence and in the presence of increasing concentrations of the test compound. To evaluate the occurrence of proteoglycan degradation, the incubation medium is collected and applied for gel filtration on Sepharose 6B columns (0.9×30 cm). Fractions (0,2 ml) are eluted with PBS at a flow rate of 5 ml/h and counted for radioactivity. The excluded volume ($V_o$) is marked by blue dextran and the total included volume ($V_t$) by phenol red. Degradation fragments of HS side chains are eluted from Sepharose 6B at $0.5<K_{av}<0.8$ (peak II). Under the reported experimental conditions, good heparanase inhibitors inhibit fragmentation of HS at concentrations of 10 µg/ml or less.

The results are shown in Table 1, below.

TABLE 1

Heparanase inhibition at dose ranging from 25 □g/ml to 5 □g/ml

| | Dose | Inhibition | | |
| --- | --- | --- | --- | --- |
| | | 25 □g/ml | 10 □g/ml | 5 □g/ml |
| | Heparin | 100% | n.d. | >100% |
| ST1516 | Heparin 40% RO | 100% | n.d. | >85% |
| ST1514 | Heparin ~50% RO | 100% | 100% | >85% |
| ST1515 | Heparin 27.5% RO | 100% | 100% | 100% |
| ST1518 | 50% NAc heparin 30% RO | 100% | 100% | >85% |

Worthy to be noted, ST1518 has a high inhibition activity even at the concentration of 1 µg/ml.

The compounds according to the present invention, and in particular new one, were tested for their activity with respect to FGF's growth factors, with the same experimental model as described in WO 01/55221 and showed an activity comparable with the ones disclosed in the cited reference.

The following examples further illustrate the invention.

EXAMPLE 1

ST1518

An excess of pyridine was added to an aqueous solution of 1 g of heparin, previously eluted from a column of Amberlite IR 120. The solution was evaporated under reduced pressure; the resulting pyridine salt of the heparin was dissolved in 50 ml of a mixture of DMSO/$H_2O$ 95:5 and stirred at 20° C. for 2 hours, in order to obtain a desulphation degree of about 50%.

Then, the solution was diluted with an equal volume of a saturated solution of $NaHCO_3$. The solution was dialysed against distilled water in membranes (cut-off 1000-2000D). The final product was isolated by evaporation under reduced pressure.

N-acetylated heparin was prepared by N-acetylation of 50% N-desulphated heparin. 1 g of heparin was dissolved in 10 ml of distilled water; the solution was cooled to 4° C. and saturated with sodium hydrogen carbonate; 625 µl of acetic anhydride were added to this solution and the mixture was stirred for 2 hours at 4° C. During the reaction, pH was controlled and maintained at about 8 by adding sodium hydrogen carbonate. Then, the solution obtained was dialysed against distilled water in membranes (cut-off 2000-1000 D).

1 g of heparin 50% N-acetylated heparin is dissolved in 25 ml of distilled water and cooled to 4° C. after the addition of 25 ml of a solution of $NaIO_4$ 0.2 M, the solution is left to stir in the dark for 20 hours, and the reaction is stopped by adding ethylene glycol and the salts are eliminated by tangential ultrafiltration. 400 mg of $NaBH_4$, subdivided in several portions, are added to the desalted solution. The solution is left to stir for 3 hours at ambient temperature, then neutralized with diluted HCl and desalted by tangential ultrafiltration.

Figure 1:
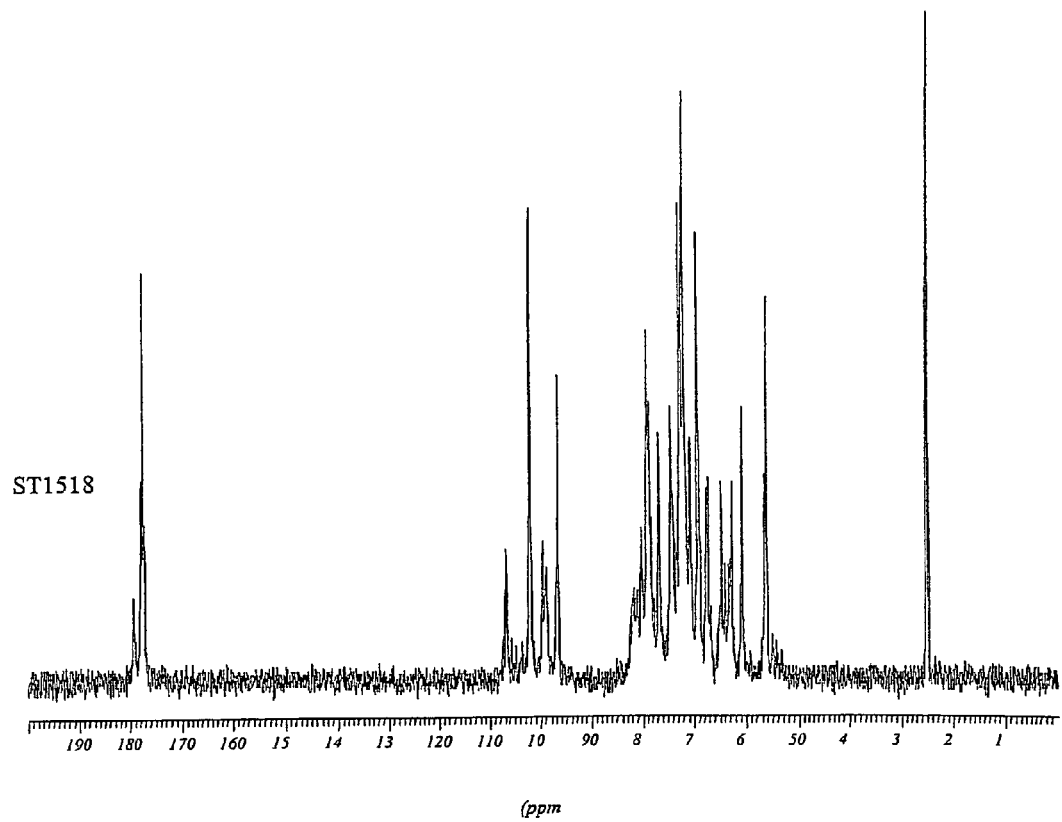
FIG. 1 is a graph of the NMR spectroscopy of the compound ST1518 a partially N-desulphated and N-reacetylated heparin.

The $^{13}C$ NMR spectrum of the compound is shown in FIG. 1.

EXAMPLE 2

ST2010 and ST2184

5 g of heparin is dissolved in 63 ml of a solution NaOH 1N. The solution is left to stir for 45 min at 60° C., cooled and neutralized with diluted HCl. Then, the solution was stirred for 48 h at 70° C., cooled and dialysed against water in membranes (cut-off 2000-1000 D).

2 g of 2-O-desulphated heparin is dissolved in 50 ml of distilled water and cooled to 4° C. after the addition of 50 ml of a solution of $NaIO_4$ 0.2 M, the solution is left to stir in the dark for 20 hours, and the reaction is stopped by adding ethylene glycol and the salts are eliminated by tangential ultrafiltration. 800 mg of $NaBH_4$, subdivided in several portions, are added to the desalted solution. The solution is left to stir for 3 hours at ambient temperature, then neutralized with diluted HCl and desalted by tangential ultrafiltration.

400 mg of oxidated-reduced heparin are dissolved in 25 ml of distilled water. After the addition of 7 mg $NaNO_2$, the pH is adjusted to 2 with diluted HCl, and the solution is left to stir for 17 min at 4° C. The reaction is stopped by neutralization. 60 mg of $NaBH_4$, subdivided in several portions, are added to the desalted solution. The solution is left to stir for 3 hours at ambient temperature, then neutralized with diluted HCl and fractionated by gel filtration. Two fractions with different molecular weights were isolated: ST2010 having a Mw=3050 and ST2184 having a Mn=5800, Mw=7520.

Figure 2:
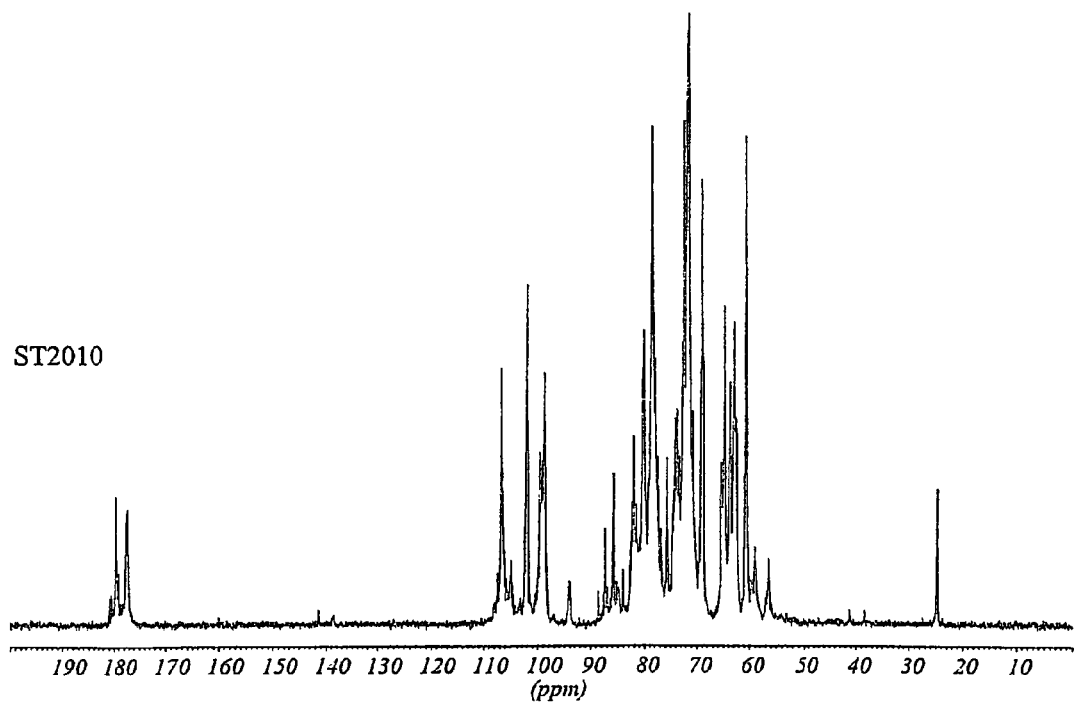
FIG. 2 is a graph of the NMR spectroscopy of the compound ST2010 an LMW heparin partially 2-O-desulphated.

The $^{13}$C NMR spectrum of the compound ST2010 is shown in FIG. 2.

EXAMPLE 3

ST2041

An excess of pyridine was added to an aqueous solution of 2 g of heparin, previously eluted from a column of Amberlite IR 120. The solution was evaporated under reduced pressure; the resulting pyridine salt of the heparin was dissolved in 100 ml of a mixture of DMSO/H$_2$O 95:5 and stirred at 20° C. for 4 hours, in order to obtain a desulphation degree of about 64%.

Then, the solution was diluted with an equal volume of a saturated solution of NaHCO$_3$. The solution was dialysed against distilled water in membranes (cut-off 1000-2000D). The final product was isolated by evaporation under reduced pressure.

Figure 3:
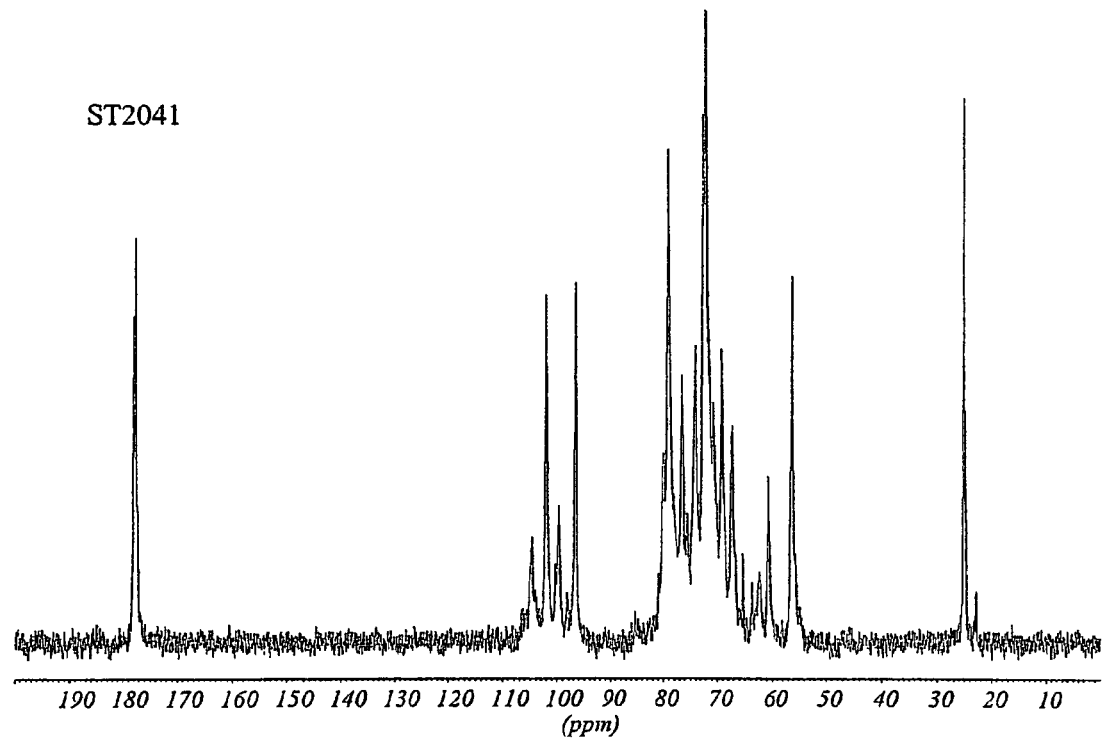
FIG. 3 is a graph of the NMR spectroscopy of the compound ST2041 a partially N-desulphated and N-reacetylated heparin.

The $^{13}$C NMR spectrum of the compound ST2041 is shown in FIG. 3.

EXAMPLE 4

Materials and Methods

Materials—All chemicals were of reagent grade from Sigma Aldrich Chemicals and used as supplied. Heparins were commercial preparations from pig mucosa (H-1 to H-3 from LDO, Trino Vercelese, Italy, and H-6 from Hepar), from beef mucosa (H-4 and H-5, LDO), and from beef lung (H-7, Upjohn, Kalamazoo, USA). The corresponding contents of major sulfate groups, as evaluated by 13C NMR spectroscopy (4) and expressed as mole percent of IdoA2SO3, GlcNSO3, and GlcN(SO3 or Ac)6SO3 per disaccharide unit, were: H-1: 69, 89, 79; H-2: 68, 85, 82; H-3: 64, 85, 82; H-4: 62, 89, 60; H-5: 66, 92, 60; H-6: 65, 86, 82; and H-7: 86, 98, 95. The average molecular weights (Mw, in Da, by GPCHPLC) were: H-1: 14,200; H-2: 18,100; H-3:19,600; H-4: 18,800; H-5: 18,200; H-6: 23,200; and H-7: 21,600. Sample desalting was carried out by dialysis against water with 1000 Da cut-off tubes or by fractionation on a 2.5×100 cm Sephadex G-25 column (Pharmacia), using 10% ethanol in water as eluent and UV detection at 210 nm. Molecular weight determinations were performed by GPC-HPLC on a Viscotex instrument equipped with VE1121 pump, Rheodyne valve 100 µl and TDA (Triple Detector Array) 302 equipped with IR, viscosimeter and 90° light scattering systems. Two 300×7.8 mm TSK GMPWXL Viscotek columns were used, with 0.1M NaNO3 as eluent (flow 0.6 ml/min). Samples were dissolved in the eluent solution at the concentration of 15 mg/ml. NMR spectra were recorded at 500 MHz for 1H and 125 MHz for 13C with a Bruker AMX spectrometer, equipped with a 5-mm 1H/X inverse probe. The spectra were obtained at 45° C. from D2O solutions (15 mg/0.5 ml D2O, 99.99% D). Chemical shifts, given in parts per million downfield from sodium-3-(trimethylsilyl)-propionate, were measured indirectly with reference to acetone in D2O (δ2.235 for 1H and δ 30.20 for 13C). The 13C NMR spectra were recorded at 300 or 400 MHz with a Bruker AC-300 or AMX-400 spectrometer.

Recombinant Human Heparanase

Recombinant enzymatically active heparanase was purified from heparanase-transfected CHO cells (1).

Preparation of Heparin Derivatives

6-O-desulfated Heparins

Procedure A: an extensively 6-O-desulfated heparin also partially (~15%) 2-O-desulfated (71 6OdeS-H [A], where the superscript denotes the degree of 6-O-desulfation), Mw 16,000, was prepared according to Nagasawa et al (5), starting from the pyridinium salt of heparin H-1, under solvolytic conditions (10 mg/ml in DMSO: water 9:1) at 100° C. for 2.5 h followed by resulfation of free amino groups with sulfur trioxide/trimethylamine complex in alkaline aqueous medium (6).

Procedure B: 6-Odesulfated-heparins (77 6Odes-H [B], Mw 19,000; 73 6OdeS-H [B], Mw 17,700, and 46 6OdeS-H [B], Mw 20,400) were prepared according to Matsuo et al (7) by O-desulfation through activation with N-methyl-N-(trimethylsilyl)trifluoroacetamide (MTSTFA) or N,O-bis (trimethylsilyl)acetamide (BTSA) without N-desulfation. Heparin H-1 (200 mg) was converted into its pyridinium salt and soaked in pyridine (20 ml). After addition of 4 ml MTSTFA, the solution was heated for 4 h at 80° C. to yield 73 6OdeS-H, or for 8 h at 60° C. to yield 73 6OdeS-H. Heparin (H-1) was converted into its pyridinium salt and soaked in pyridine (30 ml) then added of 6 ml BTSA. The solution was heated for 2 h at 60° C. to yield 46 6OdeS-H.

2-O-desulfated Heparins

Procedure A: 2-Odesulfated heparin in the IdoA form [H, IdoA(A), Mw 17,700], was prepared according to Jaseja et al (8). Heparin (500 mg) was simply dissolved in 500 ml of 0.1 M NaOH and the solution was frozen and lyophilized. The residue dissolved in 500 ml distilled water was dialyzed and the product was isolated by evaporation under reduced pressure. Its 13C NMR spectrum closely corresponded to the one reported in the literature (9), indicating an essentially complete conversion of the original IdoA2SO3 residues into IdoA residues. Procedure B: 2-O-desulfated heparin in the GalA form [H, GalA(B), Mw 12,600], was prepared by a modification of methods used by Perlin (7,8), essentially as previously described (9). Heparin (500 mg) was dissolved in 10 ml of 1M NaOH, then heated at 85° C. for 1 h times. After cooling below 30° C., the solution was brought to pH 7 with 0.1 M HCl and heated at 70° C. for 48 h to give (after cooling, dialysis and freeze drying) GalA the derivative with typical 13C NMR spectrum (9).

N-Acetylated Heparins

N-acetylated heparins (xNAH, where the superscript x denotes the degree of N-acetylation as referred to total GlcN) were prepared by time-controlled N-desulfation under solvolytic conditions (5). Briefly, the pyridinium salt of heparin was stirred at 20-25° C. in DMSO: water (9:1) for different times (30, 60, 90, 100, 120 min and 8 h) in order to obtain intermediates with different degrees of N-desulfation, which upon N-acetylation with acetic anhydride in alkaline aqueous medium (NaHCO3, 4° C., 2 h) (10) gave 29NAH, Mw 22 kDa; 39NAH, Mw 21 kDa; 50NAH, Mw 21 kDa; 58NAH, Mw 21 kDa; 70NAH, Mw 22 kDa; and 8 h for 92NAH, Mw 13.7 kDa, and 100NAH, Mw 15.7 kDa.

Glycol-split Heparins and Glycol-split N-acetylated Heparins

These were prepared by exhaustive periodateoxidation and borohydride reduction of heparin and N-acetyl heparins, respectively, without (2) or with (37, 38) prior partial 2-O-desulfation. For the first series of glycol-split, N-acetyl heparins, H-1 and 29NAH, 39NAH, 50NAH, 70NAH, and 100NAH, 250 mg samples were dissolved in 6 ml H2O and the solutions were added of 6 ml 0.1 M NaIO4. The solutions were stirred at 4° C. for 16 h in the dark. The reactions were stopped adding 1 ml ethyleneglycol and the solutions were dialyzed through a 1000 Da cut-off tubes for 16 h. Solid sodium borohydride (60 mg) was added to the retentate solutions in several portions under stirring. After 2-3 h the pH was adjusted to 4 with 0.1 M HCl, and the solutions were neutralized with 0.1 M NaOH. After desalting and dialysis, the final products were recovered by freeze-drying to yield RO.H, Mw 15.7 kDa, 26NA,RO.H, Mw 17 kDa, 40NA,RO.H, Mw 16 kDa, 53NA,RO.H, Mw 11.25 kDa, 67NA,RO.H, Mw 15 kDa, and 100NA,RO.H, Mw 20.2 Kd, respectively. For the second series of N-acetylated, glycol-split heparins (NAH, gs), 250 mg samples of H-1, 29NAH, 39NAH, 58NAH, and 70NAH, were dissolved in 5 ml of 1M NaOH, then heated at 60° C. for 30 minutes. After cooling below 30° C., the solutions were brought to pH 7 with 0.1 M HCl and heated at 70° C. for 48 h to give (after cooling, dialysis and freeze drying) partial conversion of Ido2SO3 to GalA. Products were treated as described above to yield the corresponding glycol-split derivatives H52gs, Mw 11 kDa, 29NAH, 60gs, Mw 6 kDa, 43NAH, 60gs, Mw 8.5 kDa, 57NAH, 64gs, Mw 9.5 kDa, and 70NAH,59gs, Mw 9.3 kDa. The glycolsplitting (gs) percentages were evaluated by integration of the anomeric 13C NMR signals at 106.5 ppm (A) and at 102 ppm (B), corresponding to the split uronic acid residues and 2-O-sulfated iduronic acid residues, respectively; gs=[A/(A+B)]×100. Products obtained without generation of additional nonsulfated uronic acid residues had a content of glycol-split residues (mainly arising from GlCA) of 24±1% and are designated as "reduced oxyheparins" (RO.H) (2).

Products obtained by glycol-splitting of both the preexisting and the newly generated nonsulfated uronic acids (IdoA or GalA) were designated as H,xgs (or NAH,xgs if derived from N-acetyl Running Title: Heparin-derived Heparanase Inhibitors heparins), where the superscript×indicates the percentage of glycol split uronic acid.

LMW-derivatives

LMW derivatives of H-1, H44gs, and 50NAH,25gs (50NA, RO.H) were prepared by nitrous acid depolymerization of the corresponding polysaccharides (11). A solution of polysaccharide (4 g) was dissolved in 65 ml H2O, cooled at 4° C. then added of 75 mg of NaNO2 and the pH was adjusted to 2 with 0.1 M HCl. The solution was stirred at 4° C. for 20 min and then the pH was brought to 7. Solid NaBH4 (1 g) was added in several portions under stirring. After 2-3 h, the pH was adjusted to 4 with 0.1 M HCl and the solution was neutralized with 0.1 M NaOH.

The products (LMW H-1, 6.5 kDa; LMW-H,49gs, 6.3 kDa; LMW-H, 49gs, 3.0 kDa; 50NA,RO.H, 5.4 kDa) obtained by precipitation with 3 volumes of ethanol, were dissolved in water and recovered by freeze-drying. The depolymerization degrees (DP) and the corresponding molecular weight values were determined by integration of the 13C NMR signals at 98-107 ppm and 82, 85 and 87 ppm, corresponding to total C1 and C2, C3 and C5 of the anhydro-mannitol unit, respectively. The percentage of glycol-splitting, expressed as glycol split residues referred to total uronic acids, was evaluated by integration of the 13C NMR signals at 106.5 ppm and 102 ppm, corresponding to C1 of the split uronic residues and 2-O-sulfated iduronic residues, respectively.

Cells

Cultures of bovine corneal endothelial cells were established from steer eyes and maintained in DMEM (1 g glucose/liter) supplemented with 5% newborn calf serum, 10% FCS and 1 ng/ml FGF-2, as described (1, 12). Confluent cell cultures were dissociated with 0.05% trypsin and 0.02% EDTA in phosphate buffered saline (PBS) and sub-cultured at a split ratio of 1:8 (12).

Preparation of Dishes Coated with ECM

Bovine corneal endothelial cells were plated into 35-mm tissue culture dishes at an initial density of $2 \times 10^5$ cells/ml and cultured as described above, except that 4% dextran T-40 was included in the growth medium (1, 52). On day 12, the sub-endothelial ECM was exposed by dissolving the cell layer with PBS containing 0.5% Triton X-100 and 20 mM NH4OH, followed by four washes with PBS (12). The ECM remained intact, free of cellular debris and firmly attached to the entire area of the tissue culture dish. To produce sulfate labelled ECM, Na2SO4 (Amersham, Buckinghamshire, UK) was added (25 µCi/ml) on days 2 and 5 after seeding and the cultures were incubated with the label without medium change and processed as described (1, 52). Nearly 80% of the ECM radioactivity was incorporated into HSPG.

Heparanase Inhibition Activity

Heparin species were tested for their ability to inhibit heparanase, using metabolically sulfate labeled ECM as a substrate. Briefly, sulfate labeled ECM coating the surface of 35-mm culture dishes was incubated (4 h, 37° C., pH 6.0) with recombinant human heparanase (40 ng/ml) in the absence and presence of different concentrations (0.2-1.0-5.0 µg/ml) of each heparin species. The reaction mixture contained: 50 mM NaCl, 1 mM DDT, 1 mM CaCl2, and 10 mM buffer Phosphate-Citrate, pH 6.0. To evaluate the occurrence of proteoglycan degradation, the incubation medium was collected and applied for gel filtration on Sepharose 6B columns (0.9× 30 cm). Fractions (0.2 ml) were eluted with PBS at a flow rate of 5 ml/h and counted for radioactivity. The excluded volume (Vo) was marked by blue dextran and the total included volume (Vt) by phenol red. Nearly intact HSPG are eluted from Sepharose 6B just after the void volume (Kav<0.2, fractions 1-10), while HS degradation fragments are eluted toward the Vt of the column (peak II, 0.5<Kav<0.8, fractions 15-35). Labeled fragments eluted in peak II were shown to be degradation products of HS, as they were 5-6 fold smaller than intact HS chains of HSPGs, resistant to further digestion with papain and chondroitinase ABC, and susceptible to deamination by nitrous acid. Heparanase activity=Kav×total cpm in peak II. Recovery of labeled material applied on the column ranged from 85 to 95% in different experiments. Each experiment was performed at least 3 times and the variation in elution positions (Kav values) did not exceed±15%.

Release of ECM-bound FGF-2

ECM-coated wells (four well plates) were incubated with iodinated FGF-2 (1-2×105 cpm/ng, 1.5-2.5×104 cpm per 0.25 ml/well, 3 h, 24° C.), and the unbound FGF-2 was removed by four washes with PBS containing 0.02% gelatine. The ECM was then incubated (3 h, 24° C.) with the various heparins and modified heparins, and aliquots of the 0.25 mL incubation medium were counted in a gamma counter to determine the amount of released material. The remaining ECM was washed twice with PBS, solubilized with 1 N NaOH, and the radioactivity was counted in a gamma-counter. The percentage of released 125I-FGF-2 was calculated from the total ECM-associated radioactivity. "Spontaneous" release of 125I-FGF-2 in the presence of incubation medium alone was 7-12% of the total ECM-bound FGF-2. Each experiment was performed 3-5 times, yielding similar results.

Stimulation of FGF-2 Mitogenic Activity

A cytokine-dependent, heparan sulfate deficient, lymphoid cell line (BaF3) engineered to express FGFR1 (13, 14) was applied to investigate the effect of heparin derivatives on FGF-2 mediated cell proliferation. These cells (clone F32) respond to FGF-2 only in the presence of exogenously added heparin, HS, or some modified species of heparin. Briefly, F32 cells (2×104/well) were plated into 96-well microtiter plates in the presence of 2.5 or 5.0 ng/ml FGF-2 and increasing concentrations of the test compound, in a total volume of 250 µl. Forty eight h later, 1 µCi of 3H thymidine was added per well, the cells were incubated for additional 6 h and collected with a cell harvester. Incorporated thymidine was determined by liquid scintillation counting using a topCount microplate counter (13, 14).

Gel permeation analysis of N-acetyl heparin (NAH) and ~50% glycol-split heparin (H, 52gs) before and after digestion with heparinase 2 mg of each compound were incubated for 48 h at 37° C. in 40 mM phosphate-citrate buffer, pH 5.8, with or without 4 µg recombinant heparanase in a total volume of 50 µl. The samples were lyophilized, then redisolved in 0.5 ml of water and analyzed by GPC-HPLC using 300×7.8 mm TSK PW 2000 and PW 3000 columns.

Preparation (and Schematic Presentation) of Chemically Modified Species of Heparin.

The relationship between sulfation patterns and heparanase-inhibiting activity of heparin species with unmodified backbone was studied using O-desulfated heparin derivatives and N-desulfated, N-acetylated heparins of various degrees of substitution prepared starting from a well characterized pig mucosal heparin (H-1), using established procedures with slight modifications.

6-O-Desulfation was accomplished using two different procedures, the first (A) involving solvolytic desulfation (5) and the second (B) through activated silyl acetamides (7). As reported (7), attempts to obtain extensively 6-Odesulfated heparins using procedure A involved also partial 2-O-desulfation (10-15%, by NMR analysis). Therefore, the extensively 6-Odesulfated heparin H, 77Odes was obtained only via procedure B. 2-O-Desulfation of heparin was also performed using two different procedures, leading to different products. The first procedure (A), involving lyophilization of alkaline solutions, quantitatively removes the 2-OSO3 groups retaining the IdoA residues in their original configuration (8). The second one (B), which involves heating of alkaline solutions, is more easily controlled in order to generate also partially 2-O-desulfated heparins (3) and to convert the 2-O-sulfated L-IdoA residues into D-GalA residues (7-8). Glycol-split derivatives were prepared by periodate oxidation/borohydride reduction of both unmodified heparin and partially 2-O-desulfated heparins as previously described (3). The same procedure was applied to obtain glycol-split derivatives of N-acetyl heparins of various degrees of N-acetylation and 2-O-desulfation.

All compounds were analyzed by mono- and two-dimensional, 1H and 13C NMR spectroscopy (3). Analytical data, expressed as relative molar content of 6-OSO3, 2-OSO3, and NSO3 groups are summarized in Table 2.

Superscripts on abbreviations for 6-O-desulfated (6OdeS), 2-O-desulfated (2OdeS), N-acetylated (NA) and glycol-split (gs) heparins, represent relative percentages of 6-O- and 2-O-desulfation, N-acetylation, and glycol splitting, respectively.

Heparanase inhibition by heparin derivatives

Figure 4:
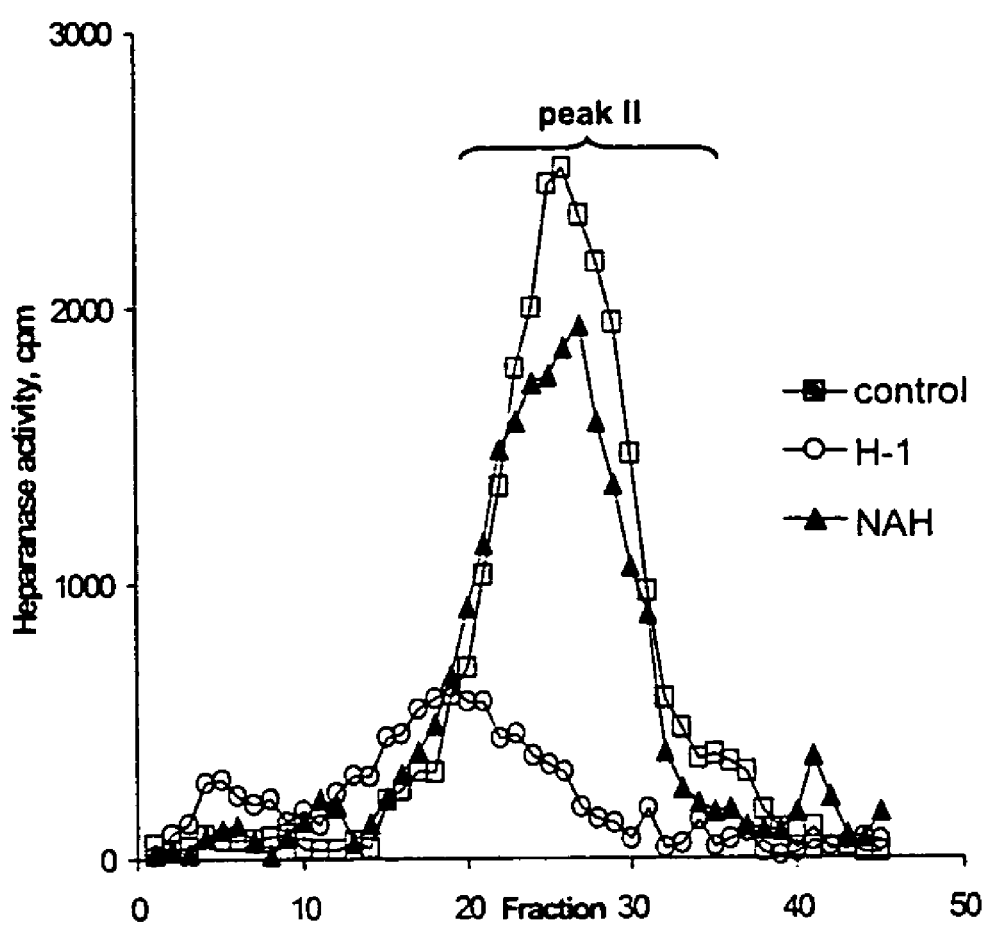
FIG. 4 is a graph representative heparanase-inhibition curves for heparin and N-acetyl heparin. Sulfate labeled ECM was incubated (4 h, 37° C., pH 6.0) with recombinant human heparanase (40 ng/ml) in the absence (control) and presence of 1 μg/ml heparin (H-1) or N-acetyl heparin (NAH). Sulfate labelled degradation fragments released into the incubation medium were analyzed by gel filtration on Sepharose 6B. The figure shows Peak II (corresponding to fractions 20-35) used to calculate percent residual activity of the enzyme (see later).

Typical heparanase-inhibition curves, showing the gel filtration profiles of sulfate labeled degradation fragments released by heparanase from metabolically labeled ECM in the absence (control) and presence of 1 µg/ml of unmodified heparin and fully N-acetylated heparin are presented in FIG. 4. Inhibition is reflected by the decreased amounts and Kav values of HS fragments released from ECM and eluted as peak II (fractions 20-35), in comparison with control incubation of the ECM with recombinant heparanase in the absence of inhibitors.

Heparanase activity is calculated as the total amount of cpm eluted in peak II multiplied by the Kav (i.e., elution position) of these fragments. The heparanase inhibitory activity (expressed as percent inhibition of heparanase) of almost all heparins at concentrations of 5, 1, and 0.2 µg/ml, is shown in Table 2. Most of the data represent the average of several separate experiments (numbers indicated). Standard deviations, indicated for each heparin, were usually lower than 5 for the most active compounds and did not exceed 20 as a mean for the less effective ones.

Figure 5:
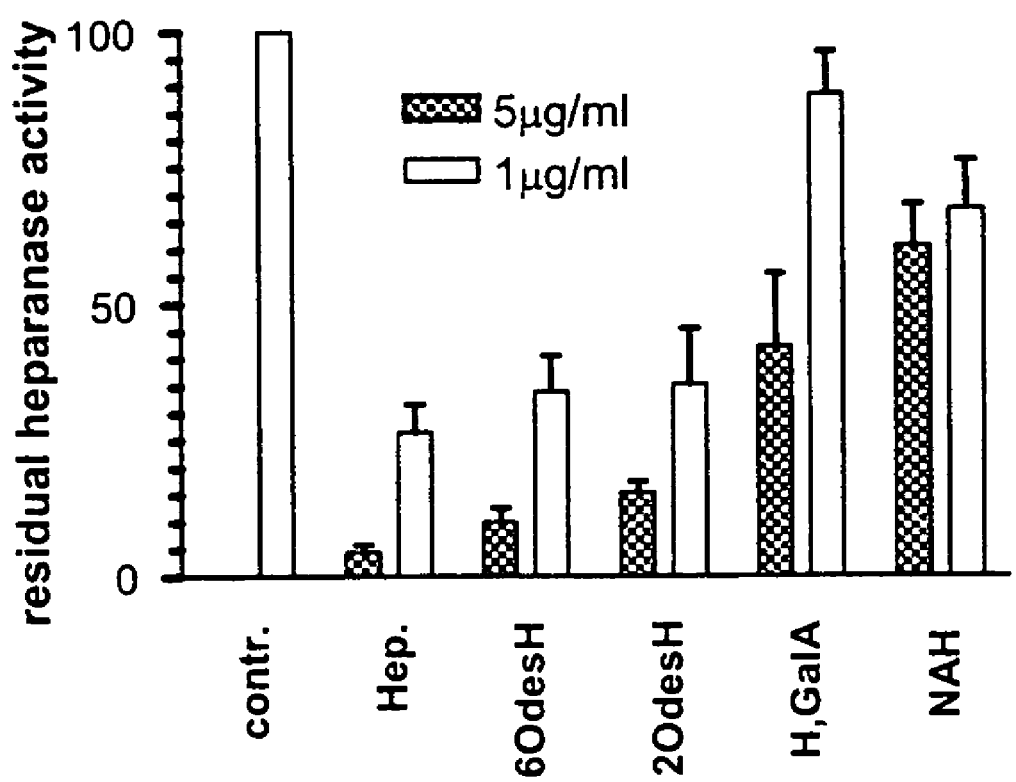
FIG. 5 represents heparanase inhibitory activity of O-desulfated species of heparin. Sulfate labeled ECM was incubated (4 h, 37° C., pH 6.0) with recombinant heparanase (40 ng/ml) in the absence (contr) and presence of 1 (white bars) or 5 (dashed bars) μg/ml unmodified heparin (H-1), NAH, or each of the indicated specifically desulfated heparins (6OdeS-H; 2OdeS-H; H, GalA). Sulfate labeled degradation fragments released into the incubation medium were analyzed by gel filtration on Sepharose 6B. Kav of peak II (see FIG. 4), calculated for each compound, was multiplied by the total cpm eluted in peak II. Results are presented as % of control. Residual heparanase activity=Kav×total cpm in peak II (% of control).

Data in Table 2 confirm that heparin is a strong inhibitor of heparanase (~70% inhibition at 1 µg/ml). No significant differences in inhibitory activity were found among H-1 and other heparin preparations from pig mucosa, beef mucosa, and beef lung (data not shown) in spite of significant differences in their sulfation patterns. Also, activity differences found between the parent heparin and its low-molecular weight species as well as between glycol-split 50NAH and its LMW species were not significant. On the other hand, well defined significant differences in heparanase-inhibiting activity were associated with specific chemical modifications of heparin. As illustrated in FIG. 5, whereas either 6-O-desulfation or 2-Odesulfation with retention of L-IdoA configuration had little or no effect on the heparanase inhibitory activity of heparin, 2-O-desulfation with change of configuration of the L-IdoA residues to L-GalA markedly decreased the inhibitory activity of heparin.

Figure 6:
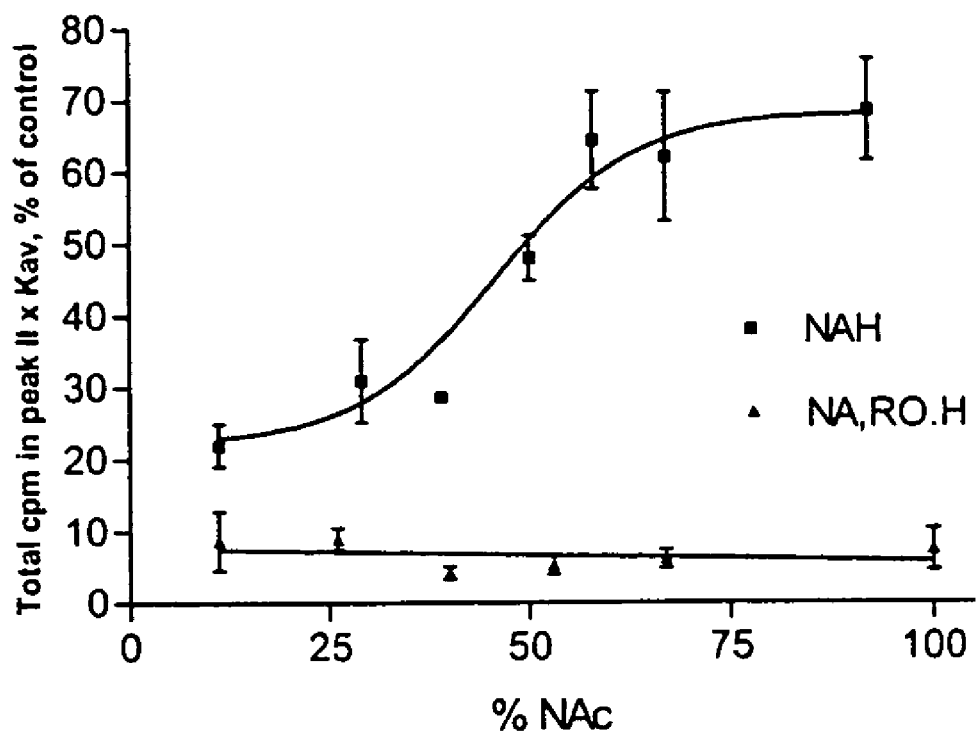
FIG. 6. Inhibition of heparanase by N-acetyl heparins and the corresponding 25% glycol-split (RO) derivatives. Sulfate labeled ECM was incubated (4 h, 37° C., pH 6.0) with heparanase (40 ng/ml) in the presence of 1 μg/ml N-acetyl heparins (NAH) with increased percentage of N-acetylation (% NAc), or with the corresponding 25% glycol-split derivatives (NA, RO.H). Sulfate labeled material released into the incubation medium was analyzed by gel filtration and heparanase enzymatic activity (Kav×total cpm in peak II) is presented as % of the 100% activity obtained in the absence of inhibitor.
Figure 7:
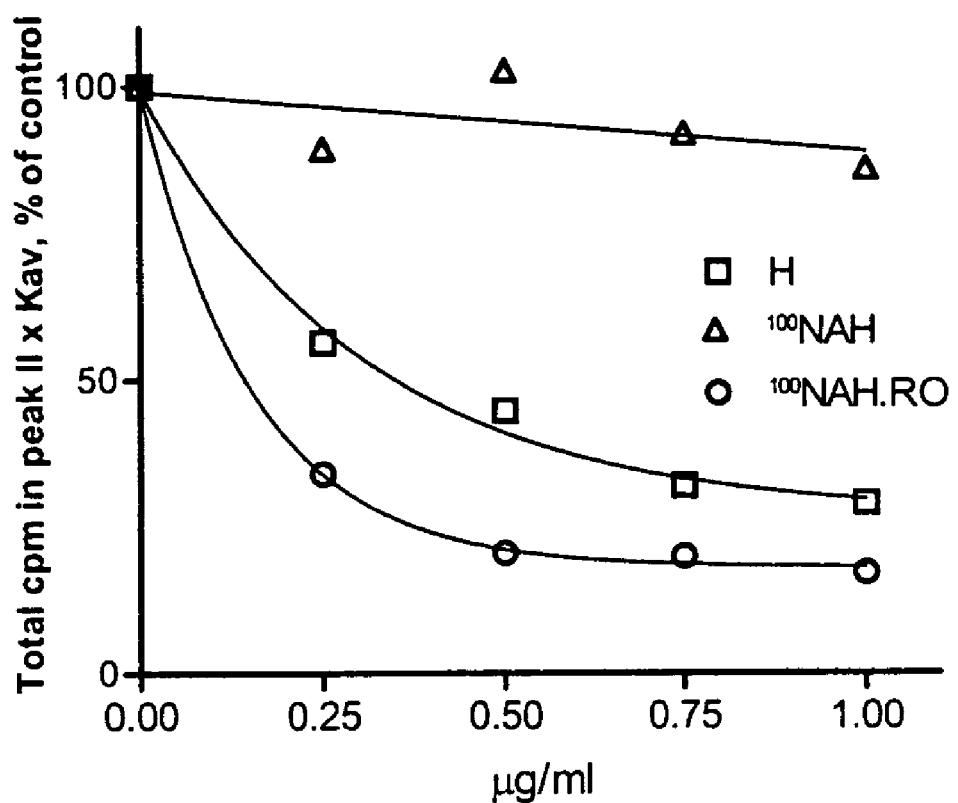
FIG. 7. Dose-dependence of heparanase-inhibition by heparin, N-acetyl heparin, and 25% glycolsplit (RO)N-acetyl heparin. Sulfate labeled ECM was incubated (4 h, 37° C., pH 6.0) with heparinase (40 ng/ml) in the absence or presence of increasing concentrations of heparin (H), 100% N-acetyl heparin (100NAH), or the corresponding 25% glycol-split (RO), 100% N-acetyl heparin (100NA, RO.H). Sulfate labeled material released into the incubation medium was analyzed by gel filtration. Heparanase enzymatic activity (total cpm in peak II×Kav) is presented as % of the activity (100%) obtained in the absence of heparin.

Also, complete removal of N-sulfate groups followed by N-acetylation resulted in a substantial decrease of the inhibitory activity (FIG. 5). However, as illustrated in FIG. 6, this effect was only noted for N-acetylation degrees higher than approximately 50%. On the other hand, glycol-splitting markedly increased the heparanase-inhibiting activity of both heparins and N-acetylated heparins and restored the inhibitory effect lost upon N-acetylation of heparin (FIG. 6 and Table 2). This effect is illustrated in FIG. 6 and Table 2 for N-acetylated heparins of the RO-type (i.e., 25% glycol-split), which almost completely inhibited the heparanase activity (to less than 10% of the control at 1 µg/ml and to 20-30% at 0.2 µg/ml), irrespective of their degree of N-acetylation. Glycol-splitting extended to newly generated non-sulfated IdoA/GalA residues in heparin and N-acetylated heparins gave products showing high heparanase inhibitory activity. The dose-dependence of the heparanase inhibitory activity is illustrated in FIG. 7 for heparin (H), fully N-acetylated heparin and its RO derivative.

Figure 8:
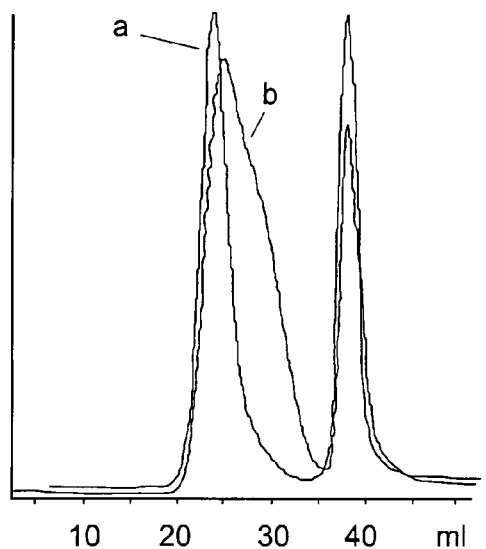
FIG. 8. Glycol-splitting inhibits cleavage by heparanase. Gel filtration profiles of fully N-acetylated heparin (A) and 52% glycol split heparin (B) before (a) and after (b) incubation with heparanase. 2 mg of each compound were incubated for 48 h at 37° C. in 40 mM phosphate-citrate buffer, pH 5.8, with or without 4 μg recombinant heparanase in a total volume of 50 μl. The samples were lyophilized, then redissolved in 0.5 ml water and analyzed by GPC-HPLC using 300×7.8 mm TSK PW 2000 and PW 3000 colums and a refraction index detector. The sharp peak is from salts.
Figure 8:
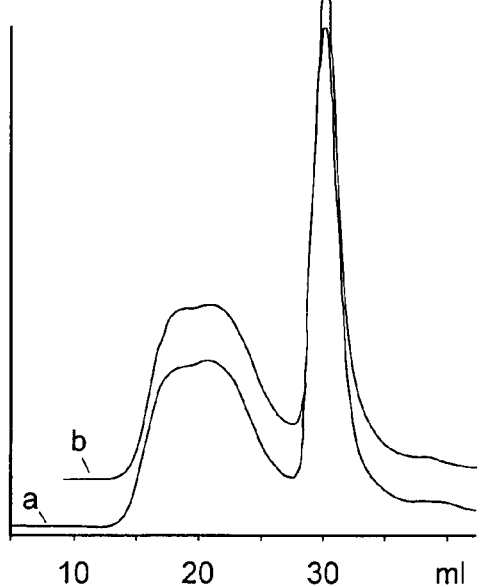

IC50 values calculated from the corresponding curves are ~5 µg/ml for NAH, ~0.4 µg/ml for H-1, and ~0.2 µg/ml for 100NA, RO.H. Gel permeation chromatographic analysis of some products of heparanase digestion, performed under conditions of the enzyme inhibition assay, indicated that whereas heparin (not shown) and N-acetyl heparin are cleaved by heparanase (as previously shown for heparin), their glycol-split derivatives are not susceptible to cleavage, as illustrated for fully N-acetylated, RO.heparin in FIGS. 8A and 52% glycol-split heparin (H,52gs) in FIG. 8B.

Figure 9:
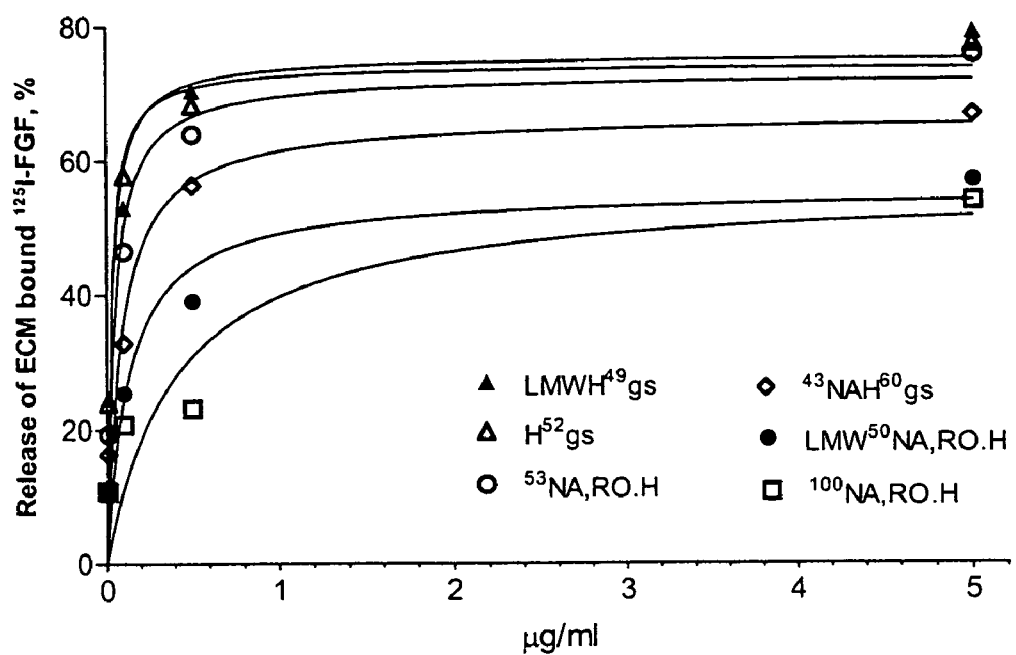
FIG. 9. Effect of combined N-acetylation and glycol-splitting on release of ECM-bound FGF-2. ECM-coated wells were incubated (3 h, 24° C.) with iodinated FGF-2 and the unbound FGF-2 was washed away, as described in "Experimental Procedures". The ECM was then incubated (3 h, 24° C.) with the indicated species of N-acetyl and glycol-split heparins and aliquots of the incubation medium were counted in a gamma counter. The remaining ECM was solubilized and its radioactivity counted and used to calculate the percentage of ECM-bound 125I-FGF-2 released by each compound.

Effect of modified heparins on release of ECM-bound FGF-2 and stimulation of FGF-2 mitogenic activity—Some of the heparin derivatives were tested for their capacity to release FGF-2 from ECM. As demonstrated in FIG. 9, dose-response curves of the FGF-2-releasing activity of glycol-split heparin (H,52gs) and its corresponding low-molecular weight derivative (LMW-H,49gs) were almost superimposable to those reported for heparin, indicating that glycol-splitting does not substantially modify the FGF-2-releasing properties of heparin. Also, the curves of the RO derivative and of heparin are superimposable (data not shown). FIG. 9 also shows that glycol-split, N-acetylated heparins behave similarly to non glycolsplit NAH in that they release ECM-bound FGF-2 consistently less than unmodified heparin.

100NAH (not shown) and 100NA,RO.H exhibited the lowest FGF-2 releasing activity among the tested compounds, yielding only about twice the spontaneous release observed in presence of the buffer (PBS) alone.

The ability of heparin, 100NAH and 100NA,RO.H to promote the mitogenic activity of recombinant FGF-2 was investigated using a cytokine-dependent, heparan sulfate deficient, lymphoid cells (BaF3) engineered to express FGFR1 (13, 14). Unlike heparin, both fully N-acetylated heparin (100NAH) and its glycol-split counterpart molecule (100NA, RO.H) failed to stimulate the mitogenic activity of FGF-2, beyond the basal level obtained in the absence of added heparin (FIG. 10). Thus, while glycol splitting of NAH fully restored its heparanase-inhibiting activity, it failed to induce a similar restoration of the ability to displace ECM-bound FGF-2 and to stimulate the mitogenic activity of recombinant FGF-2.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims

REFERENCES

Vlodavsky, I. et al. (1999) Nat. Med. 5, 793-802;
Casu, B. et al. (1985) Arzneim.-forsch. (Drug Research) 36, 637-642;
Casu, B. et al. (2004) J. Med. Chem. 47, 838-848;
Casu, B. et al. (1996) Arzneim.-Forsch. (Drug Res.) 46, 472-477;
Nagasawa, K. et al. (1977) Carbohydr. Res. 58, 47-55;
Lloyd, A. G. et al. (1971) Biochem. Pharmacol. 20, 637;
Matsuo, M. et al. (1993) Carbohydr. Res. 241, 209-215;
Jaseja, M. et al. (1989) Can. J. Chem. 67, 1449-1456;
Piani, S. et al. (1993) J. Carbohydr. Chem. 12, 507-521;
Levvy, G. A., and McAllan, A. (1959) Biochem. J. 73, 127-159;
Cifonelli, J. C. (1968). Carbohydr. Res. 8, 233-242;
Vlodavsky, I. (1999) In Current protocols in Cell Biology Vol. 1 pp. 10.14.11-10.14.14, John Wiley & Sons, New York
Ornitz, D. M. (1992) Mol. Cell. Biol. 12, 240-247;
Miao, H-Q. et al. (1997) J. Clin. Invest. 99, 1565-1575.

TABLE 2

Distribution of sulfate groups and heparanase inhibitory activity of heparin and derivatives

| | $SO_3$ groups (mole) % | | | Heparanase inhibitory activity, % | | |
|---|---|---|---|---|---|---|
| | | | | 5 µg/ml | 1 µg/ml | 0.2 µg/ml |
| | NS | A6OS | I2OS | Mean [SD (N)] | Mean [SD (N)] | Mean [SD (N)] |
| HEPARIN H-1 | 89 | 79 | 69 | 95.4 [3.7 (4)] | 73.5 [13.5 (7)] | 37.2 [20.2 (5)] |
| 6-O-DESULFATED H-1 | | | | | | |
| H, $^{71}$6OdeS (A) | 81 | 29 | 55 | 78.9 [14.2 (4)] | 50.5 [25.6 (7)] | 31.3 [31.5 (6)] |
| H, $^{77}$6Odes (B) | 87 | 23 | 67 | 93.4 | 66.0 [9.4 (2)] | 16.6 |
| H, $^{73}$6OdeS (B) | 78 | 27 | 64 | 88.9 [2.6 (2)] | 70.9 [18.0 (3)] | 44.9 [36.0 (2)] |
| H, $^{46}$6OdeS (B) | 82 | 56 | 68 | 79.9 [8.4 (3)] | 63.4 [17.0 (6)] | 35.9 [32.6 (5)] |
| 2-O-DESULFATED H-1 | | | | | | |
| H, IdoA (A) | 83 | 85 | | 98.6 [3.3 (3)] | 64.7 [17.8 (3)] | 35.6 |
| H, GalA (B) | 86 | 74 | 0 | 57.8 [18.9 (2)] | 11.5 [11.0 (2)] | 16.7 |
| N-DESULFATED, N-ACETYLATED H-1 | | | | | | |
| $^{29}$NAH | 71 | 80 | 72 | 91.9 [3.3 (3)] | 88.1 [11.6 (4)] | <15 |
| $^{39}$NAH | 61 | 80 | 71 | 78.9 [4.2 (2)] | 76.6 [7.4 (2)] | |
| $^{50}$NAH | 50 | 79 | 70 | 87.0 [13.0 (2)] | 52.0 [4.4 (2)] | <15 |
| $^{58}$NAH | 41 | 79 | 68 | 68.4 | 32.9 [15.3 (2)] | <15 |
| $^{70}$NAH | 30 | 75 | 65 | 71.3 [6.1 (3)] | 37.9 [20.2 (5)] | |
| $^{92}$NAH | 8 | 71 | 73 | 46.2 [9.6 (2)] | 32.7 [18.0 (4)] | 0 [0 (2)] |
| $^{100}$NAH | 0 | 78 | 66 | 68.4 | 32.9 [15.3 (2)] | <15 |
| GLYCOL-SPLIT H-1 | | | | | | |
| RO.H | 89 | a | 67 | 97.4 | 91.3 [5.8 (2)] | 50.3 |
| H, $^{52}$gs | 89 | a | 48 | 83.5 [7.3 (4)] | 79.1 [17.7 (6)] | 62.0 [1.6 (3)] |
| N-ACETYLATED, GLYCOL-SPLIT H-1 | | | | | | |
| $^{26}$NA, RO.H | 74 | 80 | 77 | 91.5 [2.6 (3)] | 91.1 [3.1 (4)] | 72.1 [6.0 (2)] |
| $^{40}$NA, RO.H | 60 | 80 | 71 | 100.0 | | 72.3 |
| $^{53}$NA, RO.H | 47 | 79 | 71 | 98.2 [1.8 (5)] | 94.8 [3.1 (6)] | 85.3 [6.8 (3)] |
| $^{67}$NA, RO.H | 33 | 79 | 79 | 98.5 [2.1 (2)] | 93.9 [2.2 (3)] | 84.0 [7.0 (2)] |
| $^{100}$NA, RO.H | 0 | 71 | 75 | 93.0 [4.2 (2)] | 92.5 [5.0 (3)] | 93.8 [2.6 (2)] |
| $^{29}$NAH, $^{60}$gs | 71 | a | 40 | 88.6 [0.3 (2)] | 79.6 [13.0 (2)] | 62.4 |
| $^{43}$NAH, $^{60}$gs | 57 | a | 40 | 94.5 [2.5 (2)] | 70.1 [17.1 (2)] | 72.2 [1.6 (2)] |
| $^{57}$NAH, $^{64}$gs | 42 | a | 36 | 95.1 [2.3 (2)] | 87.0 [10.5 (2)] | |
| $^{70}$NAH, $^{59}$gs | 30 | a | 41 | 92.9 [4.2 (2)] | 87.8 [12.5 (2)] | |

TABLE 2-continued

Distribution of sulfate groups and heparanase inhibitory activity of heparin and derivatives

| | SO₃ groups (mole) % | | | Heparanase inhibitory activity, % | | |
|---|---|---|---|---|---|---|
| | | | | 5 µg/ml | 1 µg/ml | 0.2 µg/ml |
| | NS | A6OS | I2OS | Mean [SD (N)] | Mean [SD (N)] | Mean [SD (N)] |
| LMW HEPARIN and DERIVATIVES | | | | | | |
| LMW-H-1 | 82 | 77 | 66 | 86 | 47.7 [35.0 (2)] | 43.1 [15.3 (2)] |
| LMW-H, $^{49}$gs | 87 | a | 51 | 95.7 [1.8 (2)] | 86.2 [2.8 (3)] | 65.8 |
| LMW-H, $^{49}$gs | 89 | a | 51 | 84.4 | 69.9 [10.0 (2)] | 73.8 |
| LMW-$^{50}$Na, gsO | 50 | 79 | 75 | 95.4 [0.6 (2)] | 90.4 [3.0 (3)] | 89.2 |

The invention claimed is:

1. A compound of formula (I)

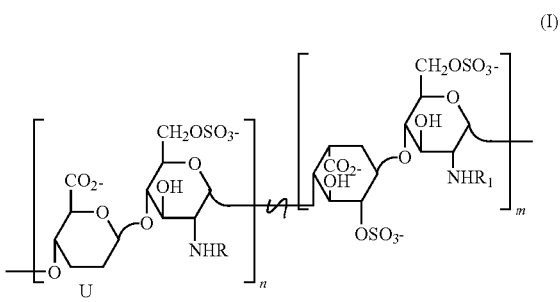

(I)

where the U ring has the following meaning

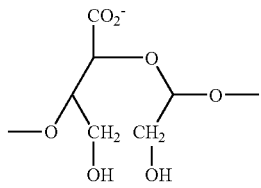

R and R₁ are an acetyl residue;

n and m, which can be the same or different, may vary from 1 to 40; the sum of m+n ranges from 6 to 40; the m:n ratio ranges from 10:2 to 1:1, the symbol /\/ indicates that units marked m and n are statistically distributed along the polysaccharide chain and are not necessarily in sequence.

2. A compound according to claim 1, which is 100% desulphated and N-reacetylated heparin with a molecular weight MW=20.2 kDa.

3. A pharmaceutical composition containing the compound of claim 1 as an active ingredient in admixture with pharmaceutically acceptable vehicles and excipients.

4. A method of inhibiting heparanase and/or inhibiting FGF growth factor comprising administering to a subject in need of said inhibition an effective amount of the compound of claim 1.

5. The method of claim 4, wherein said compound has antiangiogenic activity.

6. The method of claim 4, wherein said method is useful for the treatment of an inflammation.

7. The method of claim 4, wherein said method is useful for the treatment of a disease selected from primary tumours, metastases, diabetic rethinopathy, psoriasis, retrolenticular fibroplasia, arthritis, allograft rejection, cardiovascular diseases, fibro-proliferative disease, diseases elicited by abnormal platelet aggregation, proliferative rethinopathies, insulin dependent diabetes, inflammatory bowel disease.

8. The method according to claim 7, wherein said inflammatory bowel disease is selected from the group consisting of ulcerative colitis, and Crohn's disease.

9. The method of claim 4, wherein said method is useful for the treatment of a disease selected from the group consisting of: diseases elicited by smooth muscle proliferation, Goodpasture syndrome, acute glomerulonephritis, neonatal pulmonary hypertension, asthma, congestive heart failure, adult pulmonary hypertension, renal vascular hypertension.

10. The method of claim 4, wherein said method is useful for the treatment of restenosis after angioplasty or coronary by-pass.

* * * * *